(12) United States Patent
Chu et al.

(10) Patent No.: US 11,466,094 B2
(45) Date of Patent: Oct. 11, 2022

(54) DOSING FOR TREATMENT WITH ANTI-CD20/ANTI-CD3 BISPECIFIC ANTIBODIES

(71) Applicant: Genentech, Inc., South San Francisco, CA (US)

(72) Inventors: Yu-Waye Chu, South San Francisco, CA (US); Iraj Hosseini, South San Francisco, CA (US); Saroja Ramanujan, South San Francisco, CA (US); Kapil Gadkar, South San Francisco, CA (US); Chi-Chung Li, South San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 226 days.

(21) Appl. No.: 15/813,657

(22) Filed: Nov. 15, 2017

(65) Prior Publication Data
US 2018/0134798 A1    May 17, 2018

Related U.S. Application Data

(60) Provisional application No. 62/500,217, filed on May 2, 2017, provisional application No. 62/422,391, filed on Nov. 15, 2016.

(51) Int. Cl.
*A61K 31/573* (2006.01)
*C07K 16/28* (2006.01)
*A61K 39/395* (2006.01)
*A61K 39/00* (2006.01)

(52) U.S. Cl.
CPC ........ *C07K 16/2887* (2013.01); *A61K 31/573* (2013.01); *A61K 39/3955* (2013.01); *C07K 16/2809* (2013.01); *C07K 16/2827* (2013.01); *C07K 16/2866* (2013.01); *A61K 2039/507* (2013.01); *A61K 2039/54* (2013.01); *A61K 2039/545* (2013.01); *C07K 2317/24* (2013.01); *C07K 2317/31* (2013.01); *C07K 2317/41* (2013.01)

(58) Field of Classification Search
CPC .................................. C07K 16/2887
USPC ..................................... 424/136.1
See application file for complete search history.

(56) References Cited

U.S. PATENT DOCUMENTS

| | | |
|---|---|---|
| 5,500,362 A | 3/1996 | Robinson et al. |
| 5,624,821 A | 4/1997 | Winter et al. |
| 5,648,260 A | 7/1997 | Winter et al. |
| 5,677,171 A | 10/1997 | Hudziak et al. |
| 5,731,168 A | 3/1998 | Carter et al. |
| 5,821,337 A | 10/1998 | Carter et al. |
| 5,869,046 A | 2/1999 | Presta et al. |
| 6,194,551 B1 | 2/2001 | Idusogie et al. |
| 6,248,516 B1 | 6/2001 | Winter et al. |
| 6,455,043 B1 | 9/2002 | Grillo-Lopez |
| 6,602,684 B1 | 8/2003 | Umana et al. |
| 6,737,056 B1 | 5/2004 | Presta |
| 7,332,581 B2 | 2/2008 | Presta |
| 7,371,826 B2 | 5/2008 | Presta |
| 7,435,797 B2 | 10/2008 | Lowman et al. |
| 7,612,181 B2 | 11/2009 | Wu et al. |
| 7,682,612 B1 | 3/2010 | White et al. |
| 7,695,936 B2 | 4/2010 | Carter et al. |
| 7,799,900 B2 | 9/2010 | Adams et al. |
| 8,219,149 B2 | 7/2012 | Lafata et al. |
| 8,258,268 B2 | 9/2012 | Wu et al. |
| 8,562,992 B2 | 10/2013 | Adams et al. |
| 8,709,421 B2 | 4/2014 | Heiss et al. |
| 8,722,859 B2 | 5/2014 | Miller et al. |
| 8,895,702 B2 | 11/2014 | Williams et al. |
| 8,969,526 B2 | 3/2015 | Baehner et al. |
| 9,011,864 B2 | 4/2015 | Schulz et al. |
| 9,017,676 B2 | 4/2015 | Lindhofer |
| 9,308,257 B2 | 4/2016 | Sharma, Sr. et al. |
| 9,315,567 B2 | 4/2016 | Chang et al. |
| 9,493,563 B2 | 11/2016 | Blein et al. |
| 9,587,021 B2 | 3/2017 | Huang et al. |
| 9,657,102 B2 | 5/2017 | Smith et al. |
| 9,714,294 B2 | 7/2017 | De Goeij et al. |
| 10,357,571 B2 | 7/2019 | Williams et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0095243 A1 | 5/2005 | Chan et al. |
| 2005/0123546 A1 | 6/2005 | Umana et al. |

(Continued)

FOREIGN PATENT DOCUMENTS

| | | |
|---|---|---|
| CN | 102281902 A | 12/2011 |
| CN | 102369218 A | 3/2012 |
| CN | 101675077 B | 9/2013 |
| EP | 1870459 A1 | 12/2007 |
| EP | 1870459 A4 | 9/2010 |

(Continued)

OTHER PUBLICATIONS

Lee et al (Blood, 2014, 124(2): 188-195).*
Nishimoto et al (J Rheumatol, 2003, 30: 1426-1435).*
Buhmann et al (Bone Marrow Transplantation, 2009, 43: 383-397).*
Seung et al (Blood, 2014, 124(21):3111).*

(Continued)

*Primary Examiner* — Sean E Aeder
(74) *Attorney, Agent, or Firm* — Clark & Elbing LLP; Karen L. Elbing

(57) ABSTRACT

The invention provides methods of dosing for the treatment of cancers, such as B cell proliferative disorders, with anti-cluster of differentiation 20 (CD20)/anti-cluster of differentiation 3 (CD3) bispecific antibodies.

82 Claims, No Drawings

Specification includes a Sequence Listing.

(56) References Cited

U.S. PATENT DOCUMENTS

| | | |
|---|---|---|
| 2009/0252683 A1 | 10/2009 | Kischel et al. |
| 2009/0304719 A1 | 12/2009 | Daugherty et al. |
| 2010/0015133 A1 | 1/2010 | Igawa et al. |
| 2010/0150918 A1 | 6/2010 | Kufer et al. |
| 2010/0331527 A1 | 12/2010 | Davis et al. |
| 2011/0020322 A1 | 1/2011 | Wilkins et al. |
| 2011/0123532 A1 | 5/2011 | Gurney et al. |
| 2011/0178279 A1 | 7/2011 | Williams et al. |
| 2012/0244577 A1 | 9/2012 | Dixit et al. |
| 2012/0251531 A1 | 10/2012 | Baehner et al. |
| 2013/0129723 A1 | 5/2013 | Blankenship et al. |
| 2013/0165638 A1 | 6/2013 | Hsu et al. |
| 2013/0171095 A1 | 7/2013 | Bernett et al. |
| 2013/0266568 A1 | 10/2013 | Brinkmann et al. |
| 2013/0287774 A1 | 10/2013 | Zugmaier et al. |
| 2014/0079689 A1 | 3/2014 | Elliott et al. |
| 2014/0088295 A1 | 3/2014 | Smith et al. |
| 2014/0112914 A1 | 4/2014 | Nezu et al. |
| 2014/0170149 A1 | 6/2014 | Neijssen et al. |
| 2014/0187753 A1 | 7/2014 | Blein et al. |
| 2014/0302064 A1 | 10/2014 | Moore |
| 2014/0377270 A1 | 12/2014 | Moore et al. |
| 2015/0098900 A1 | 4/2015 | Ebens et al. |
| 2015/0133640 A1 | 5/2015 | Blein et al. |
| 2015/0166661 A1 | 6/2015 | Chen et al. |
| 2015/0266966 A1 | 9/2015 | Smith et al. |
| 2015/0284475 A1 | 10/2015 | Zhou et al. |
| 2016/0000916 A1 | 1/2016 | Crotts et al. |
| 2016/0017058 A1 | 1/2016 | Kim et al. |
| 2016/0075785 A1 | 3/2016 | Ast et al. |
| 2016/0090416 A1 | 3/2016 | Gunde et al. |
| 2016/0145339 A1 | 5/2016 | Zhou et al. |
| 2016/0152711 A1 | 6/2016 | Williams et al. |
| 2016/0159906 A1 | 6/2016 | Sun et al. |
| 2016/0194399 A1 | 7/2016 | Irving et al. |
| 2016/0368985 A1 | 12/2016 | Hotzel et al. |
| 2016/0368994 A1 | 12/2016 | Kelley et al. |
| 2017/0008971 A1 | 1/2017 | Dennis et al. |
| 2017/0022274 A1 | 1/2017 | Chang et al. |
| 2017/0158773 A1 | 6/2017 | Adams et al. |
| 2017/0204194 A1 | 7/2017 | Chen et al. |
| 2017/0209573 A1 | 7/2017 | Bacac et al. |
| 2017/0218074 A1 | 8/2017 | Williams et al. |
| 2017/0224818 A1 | 8/2017 | Lindhofer et al. |
| 2017/0267783 A1 | 9/2017 | Nezu et al. |
| 2018/0057593 A1 | 3/2018 | Dennis |
| 2018/0148508 A1 | 5/2018 | Wang et al. |
| 2018/0193479 A1 | 7/2018 | Williams et al. |
| 2020/0164077 A1 | 5/2020 | Williams et al. |
| 2020/0199578 A1 | 6/2020 | Short et al. |

FOREIGN PATENT DOCUMENTS

| | | |
|---|---|---|
| EP | 2482212 A1 | 8/2012 |
| EP | 2578230 A1 | 4/2013 |
| EP | 2647707 A1 | 10/2013 |
| EP | 2647707 A4 | 4/2014 |
| EP | 1870459 B1 | 6/2016 |
| JP | 2008-291036 A | 12/2008 |
| JP | 2009-539413 A | 11/2009 |
| JP | 2010-524435 A | 7/2010 |
| JP | 2013-515509 A | 5/2013 |
| JP | 2013-528569 A | 7/2013 |
| JP | 2013-529084 A | 7/2013 |
| JP | 2015-509951 A | 4/2015 |
| JP | 2015-509952 A | 4/2015 |
| JP | 2018-527887 A | 9/2018 |
| RU | 2539112 C2 | 1/2015 |
| TW | 201508008 A | 3/2015 |
| WO | WO-91/03493 A1 | 3/1991 |
| WO | WO-92/22653 A1 | 12/1992 |
| WO | WO-9404679 A1 | 3/1994 |
| WO | WO-94/29351 A2 | 12/1994 |
| WO | WO-96/01126 A1 | 1/1996 |
| WO | WO-96/27011 A1 | 9/1996 |
| WO | WO-97/30087 A1 | 8/1997 |
| WO | WO-98/50431 A2 | 11/1998 |
| WO | WO-98/58964 A1 | 12/1998 |
| WO | WO-98/50431 A3 | 1/1999 |
| WO | WO-99/22764 A1 | 5/1999 |
| WO | WO-99/51642 A1 | 10/1999 |
| WO | WO-00/61739 A1 | 10/2000 |
| WO | WO-01/29246 A1 | 4/2001 |
| WO | WO-02/31140 A1 | 4/2002 |
| WO | WO-03/011878 A2 | 2/2003 |
| WO | WO-03/084570 A1 | 10/2003 |
| WO | WO-03/085107 A1 | 10/2003 |
| WO | WO-03/085119 A1 | 10/2003 |
| WO | WO-2004/056312 A2 | 7/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/083431 A2 | 9/2005 |
| WO | WO-2005/100402 A1 | 10/2005 |
| WO | WO-2006/029879 A2 | 3/2006 |
| WO | WO-2007/005874 A2 | 1/2007 |
| WO | WO-2007/042261 A2 | 4/2007 |
| WO | WO-2007/110205 A2 | 10/2007 |
| WO | WO-2007/146968 A2 | 12/2007 |
| WO | WO-2008/077546 A1 | 7/2008 |
| WO | WO-2008/119566 A2 | 10/2008 |
| WO | WO-2008/119567 A2 | 10/2008 |
| WO | WO-2009/070642 A1 | 6/2009 |
| WO | WO-2009/106321 A1 | 9/2009 |
| WO | WO-2010/057109 A1 | 5/2010 |
| WO | WO-2010/077643 A1 | 7/2010 |
| WO | WO-2010/114940 A1 | 10/2010 |
| WO | WO-2011/028945 A1 | 3/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/121110 A1 | 10/2011 |
| WO | WO-2011/131746 A2 | 10/2011 |
| WO | WO-2011/143545 A1 | 11/2011 |
| WO | WO-2012/025525 A1 | 3/2012 |
| WO | WO-2012/058768 A1 | 5/2012 |
| WO | WO-2012/058768 A8 | 6/2012 |
| WO | WO-2012/073985 A1 | 6/2012 |
| WO | WO-2012075581 A1 | 6/2012 |
| WO | WO-2012123949 A1 | 9/2012 |
| WO | WO-2012/143524 A2 | 10/2012 |
| WO | WO-2012/158818 A2 | 11/2012 |
| WO | WO-2012/162067 A2 | 11/2012 |
| WO | WO-2013/128027 A1 | 9/2013 |
| WO | WO-2013128194 A1 | 9/2013 |
| WO | WO-2014/022540 A1 | 2/2014 |
| WO | WO-2014/028560 A2 | 2/2014 |
| WO | WO-2014/047231 A1 | 3/2014 |
| WO | WO-2014/028560 A3 | 5/2014 |
| WO | WO-2014/083178 A1 | 6/2014 |
| WO | WO-2014108483 A1 | 7/2014 |
| WO | WO-2014/122251 A2 | 8/2014 |
| WO | WO-2014/141152 A2 | 9/2014 |
| WO | WO-2014/144722 A2 | 9/2014 |
| WO | WO-2014/153002 A1 | 9/2014 |
| WO | WO-2014/122251 A3 | 10/2014 |
| WO | WO-2014170063 A1 | 10/2014 |
| WO | WO-2014/141152 A3 | 12/2014 |
| WO | WO-2014/191113 A1 | 12/2014 |
| WO | WO-2014-193973 A2 | 12/2014 |
| WO | WO-2014/210064 A1 | 12/2014 |
| WO | WO-2015/006749 A2 | 1/2015 |
| WO | WO-2015/013671 A1 | 1/2015 |
| WO | WO-2014/191113 A8 | 2/2015 |
| WO | WO-2015-095392 A1 | 6/2015 |
| WO | WO-2015143079 A1 | 9/2015 |
| WO | WO-2015184203 A1 | 12/2015 |
| WO | WO-2015184207 A1 | 12/2015 |
| WO | WO-2016014942 A1 | 1/2016 |
| WO | WO-2016/019969 A1 | 2/2016 |
| WO | WO-2016/020065 A1 | 2/2016 |
| WO | WO-2016/036678 A1 | 3/2016 |
| WO | WO-2016/081490 A1 | 5/2016 |
| WO | WO-2016/090210 A1 | 6/2016 |

(56) References Cited

FOREIGN PATENT DOCUMENTS

| WO | WO-2016/110576 A1 | 7/2016 |
|---|---|---|
| WO | WO-2016135239 A1 | 9/2016 |
| WO | WO-2016/179003 A1 | 11/2016 |
| WO | WO-2016/191750 A1 | 12/2016 |
| WO | WO-2016/201300 A1 | 12/2016 |
| WO | WO-2016/204966 A1 | 12/2016 |
| WO | WO-2016-205520 A1 | 12/2016 |
| WO | WO-2016/205531 A2 | 12/2016 |
| WO | WO-2017/132279 A1 | 8/2017 |
| WO | WO-2018/093821 A1 | 5/2018 |

OTHER PUBLICATIONS

Stieglmaier et al (Exp Opin on Biol Ther, 2015, 15(8): 1093-1099).*
Goebeler et al (Journal of Clinical Oncology, 2016, 34(10): 1104-1111).*
Stanglmaier et al., "Bi20 (FBTA05), a novel trifunctional bispecific antibody (anti-CD20 x anti-CD3), mediates efficient killing of B-cell lymphoma cells even with very low CD20 expression levels," Int J Cancer. 123(5):1181-9 (2008).
Anderson et al., "G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. 80(11):2826-34 (1992).
Donaldson et al., "Design and development of masked therapeutic antibodies to limit off-target effects: application to anti-EGFR antibodies," Cancer Biol Ther. 8(22); 2147-50 (2009).
Hosseini et al., "Systems pharmacology modeling of anti-CD20/ CD3 T-cell dependent bispecific antibody and its application to clinical trial design," American Conference on Pharmacometrics 7; Oct. 25; Bellevue, WA. (2016) (1 page).
Law et al., "Expression and characterization of recombinant soluble human CD3 molecules: presentation of antigenic epitopes defined on the native TCR-CD3 complex," Int Immunol. 14(4): 389-400 (2002).
Li, "Successful QSP modeling in drug development starts with the right questions," American Conference on Pharmacometrics 8, Oct. 16, Fort Lauderdale, FL. (2017) (20 pages).
Lippow et al., "Computational design of antibody affinity improvement beyond in vivo maturation," available in PMC Jan. 7, 2010, published in final edited form as: Nat Biotechnol. 25(10):1171-6 (2007) (14 pages).
Atwell et al., "Stable heterodimers from remodeling the domain interface of a homodimer using a phage display library," J Mol Biol. 270(1):26-35 (1997).
Baeuerle et al., "Bispecific T-cell engaging antibodies for cancer therapy," Cancer Res. 69(12):4941-4 (2009).
Bortoletto et al., "Optimizing anti-CD3 affinity for effective T cell targeting against tumor cells," Eur J Immunol. 32(11):3102-7 (2002).
Brüggemann et al., "Comparison of the effector functions of human immunoglobulins using a matched set of chimeric antibodies," J Exp Med. 166(5):1351-61 (1987).
Carter, "Bispecific human IgG by design," J Immunol Methods. 248(1-2):7-15 (2001).
Clynes et al., "Fc receptors are required in passive and active immunity to melanoma," Proc Natl Acad Sci U S A. 95(2):652-6 (1998).
Cragg et al., "Antibody specificity controls in vivo effector mechanisms of anti-CD20 reagents," Blood. 103(7):2738-43 (2004).
Cragg et al., "Complement-mediated lysis by anti-CD20 mAb correlates with segregation into lipid rafts," Blood. 101(3):1045-52 (2003).
Duncan et al., "The binding site for C1q on IgG," Nature. 332(6166):738-40 (1988).
Edelman et al., "The covalent structure of an entire gammaG immunoglobulin molecule," Proc Natl Acad Sci U S A. 63(1):78-85 (1969).

Gazzano-Santoro et al., "A non-radioactive complement-dependent cytotoxicity assay for anti-CD20 monoclonal antibody," J Immunol Methods. 202(2):163-71 (1997).
Guyer et al., "Immunoglobulin binding by mouse intestinal epithelial cell receptors," J Immunol. 117(2):587-93 (1976).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-502 (1985).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).
Hudson et al., "Engineered antibodies," Nat Med. 9(1):129-34 (2003).
Idusogie et al., "Mapping of the C1q binding site on rituxan, a chimeric antibody with a human IgG1 Fc," J Immunol. 164(8):4178-84 (2000).
Jager et al., "The trifunctional antibody ertumaxomab destroys tumor cells that express low levels of human epidermal growth factor receptor 2," Cancer Res. 69(10):4270-6 (2009).
Junttila et al., "Antitumor efficacy of a bispecific antibody that targets HER2 and activates T cells," Cancer Res. 74(19):5561-71 (2014).
Kanda et al., "Comparison of cell lines for stable production of fucose-negative antibodies with enhanced ADCC," Biotechnol Bioeng. 94(4):680-8 (2006).
Kiewe et al., "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005).
Kiewe et al., "Phase I trial of the trifunctional anti-HER2 x anti-CD3 antibody ertumaxomab in metastatic breast cancer," Clin Cancer Res. 12(10):3085-91 (2006).
Kim et al., "Localization of the site of the murine IgG1 molecule that is involved in binding to the murine intestinal Fc receptor," Eur J Immunol. 24(10):2429-34 (1994).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Leabman et al., "Effects of altered FcgammaR binding on antibody pharmacokinetics in cynomolgus monkeys," MAbs. 5(6):896-903 (2013).
Lum et al., "Targeting T cells with bispecific antibodies for cancer therapy," available in PMC Oct. 8, 2013, published in final edited form as: BioDrugs. 25(6):365-79 (2011) (24 pages).
Merchant et al., "An efficient route to human bispecific IgG," Nat Biotechnol. 16(7):677-81 (1998).
Metz et al., "Bispecific antibody derivatives with restricted binding functionalities that are activated by proteolytic processing," Protein Eng Des Sel. 25(10):571-80 (2012).
Moore et al., "Application of dual affinity retargeting molecules to achieve optimal redirected T-cell killing of B-cell lymphoma," Blood. 117(17):4542-51 (2011) (11 pages).

(56) References Cited

OTHER PUBLICATIONS

Nagorsen et al., "Immunomodulatory therapy of cancer with T cell-engaging BiTE antibody blinatumomab," Exp Cell Res. 317(9):1255-60 (2011).
Okazaki et al., "Fucose depletion from human IgG1 oligosaccharide enhances binding enthalpy and association rate between IgG1 and FcgammaRIIIa," J Mol Biol. 336(5):1239-49 (2004).
Pessano et al., "The T3/T cell receptor complex: antigenic distinction between the two 20-kd T3 (T3-delta and T3-epsilon) subunits," Embo J. 4(2):337-44 (1985).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Ravetch et al., "Fc receptors," Annu Rev Immunol. 9:457-92 (1991).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Ripka et al., "Two Chinese hamster ovary glycosylation mutants affected in the conversion of GDP-mannose to GDP-fucose," Arch Biochem Biophys. 249(2):533-45 (1986).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Shalaby et al., "Bispecific HER2 x CD3 antibodies enhance T-cell cytotoxicity in vitro and localize to HER2-overexpressing xenografts in nude mice," Clin Immunol Immunopathol. 74(2):185-92 (1995).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. 276(9):6591-604 (2001).
Sondermann et al., "The 3.2-A crystal structure of the human IgG1 Fc fragment-Fc gammaRIII complex," Nature. 406(6793):267-73 (2000).
Spiess et al., "Bispecific antibodies with natural architecture produced by co-culture of bacteria expressing two distinct half-antibodies," Nat Biotechnol. 31(8):753-8 (2013) (7 pages).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Westin et al., "Safety and activity of PD1 blockade by pidilizumab in combination with rituximab in patients with relapsed follicular lymphoma: a single group, open-label, phase 2 trial," Lancet Oncol. 15(1):69-77 (2014).
Wright et al., "Effect of glycosylation on antibody function: implications for genetic engineering," Trends Biotechnol. 15(1):26-32 (1997).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. 87(5):614-22 (2004).
Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).
Zhu et al., "Identification of heavy chain residues in a humanized anti-CD3 antibody important for efficient antigen binding and T cell activation," J Immunol. 155(4):1903-10 (1995).
Communication pursuant to Article 94(3) dated Apr. 10, 2017, for Chen et al., "Anti-CD3 Antibodies and Methods of Use," European Patent Application No. 14828608.1, filed Dec. 17, 2014 (7 pages).
Communication pursuant to Article 94(3) dated Nov. 8, 2017, for Chen et al., "Anti-CD3 Antibodies and Methods of Use," European Patent Application No. 14828608.1, filed Dec. 17, 2014 (11 pages).
Extended European Search Report dated May 29, 2017, for Chen et al., "Anti-CD3 Antibodies and Methods of Use," European Patent Application No. 17156352.1, filed Dec. 17, 2014 (10 pages).
International Preliminary Report on Patentability dated Dec. 19, 2017, for Hotzel et al., "Humanized and Affinity Matured Antibodies to FCRH5 and Methods of Use," International Patent Application No. PCT/US2016/037879, filed Jun. 16, 2016 (12 pages).
International Preliminary Report on Patentability dated Jun. 21, 2016, for Chen et al., "Anti-CD3 Antibodies and Methods of Use," International Patent Application No. PCT/US2014/070951, filed Dec. 17, 2014 (19 pages).
International Preliminary Report on Patentability dated Nov. 7, 2017, for Dennis, "Masked Anti-CD3 Antibodies and Methods of Use," International Patent Application No. PCT/US2016/030127, filed Apr. 29, 2016 (9 pages).
International Search Report and Written Opinion for International Patent Application No. PCT/US2017/061683, dated Feb. 23, 2018 (14 pages).
International Search Report and Written Opinion dated Aug. 3, 2016 for Dennis, "Masked Anti-CD3 Antibodies and Methods of Use," International Patent Application No. PCT/US2016/030127, filed Apr. 29, 2016 (15 pages).
International Search Report and Written Opinion dated May 28, 2015, for Chen et al., "Anti-CD3 Antibodies and Methods of Use," International Patent Application No. PCT/US2014/070951, filed Dec. 17, 2014 (33 pages).
International Search Report and Written Opinion dated Nov. 4, 2016, for Hotzel et al., "Humanized and Affinity Matured Antibodies to FCRH5 and Methods of Use," International Patent Application No. PCT/US2016/037879, filed Jun. 16, 2016 (20 pages).
Invitation to Pay Additional Fees dated Apr. 9, 2015, for Chen et al., "Anti-CD3 Antibodies and Methods of Use," International Patent Application No. PCT/US2014/070951, filed Dec. 17, 2014 (12 pages).
Invitation to Pay Additional Fees dated Sep. 12, 2016, for Hotzel et al., "Humanized and Affinity Matured Antibodies to FCRH5 and Methods of Use," International Patent Application No. PCT/US2016/037879, filed Jun. 16, 2016 (8 pages).
Notice of Reasons for Rejection dated Dec. 19, 2017, for Chen et al., "Anti-CD3 Antibodies and Methods of Use," Japanese Patent Application No. 2016-539276, filed Dec. 17, 2014 (6 pages).
Search Report dated Aug. 8, 2017, for Chen et al., "Anti-CD3 Antibodies and Methods of Use," Singaporean Patent Application No. 11201604990P, filed Dec. 17, 2014 (6 pages).
Written Opinion dated Aug. 8, 2017, for Chen et al., "Anti-CD3 Antibodies and Methods of Use," Singaporean Patent Application No. 11201604990P, filed Dec. 17, 2014 (7 pages).
Brown et al., "Tolerance to single, but not multiple, amino acid replacements in antibody VH CDR2: a means of minimizing B cell wastage from somatic hypermutation?" J Immunol. 156(9):3285-91 (1996).
Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).
Liu et al., "Improvement in soluble expression levels of a diabody by exchanging expression vectors," Protein Expr Purif. 62(1):15-20 (2008) (6 pages).
Shen et al., "Preparation and characterization for bispecific antibodies of anti-CD3 x anti-idiotype to B cell lymphocytic leukemia," J Tongji Med Univ. 19(3):166-9 (1999) (4 pages).
Brack et al., "A Bispecific HER2-Targeting FynomAb with Superior Antitumor Activity and Novel Mode of Action," Mol Cancer Ther. 13(8): 2030-39 (2014) (11 pages).
Brinkmann et al., "The making of bispecific anitbodies," MABS. 9(2): 182-212 (2017).
Choi et al., "Bispecific antibodies engage T cells for antitumor immunotherapy," Expert Opin. Biol. Ther. 11(7): 843-53 (2011).
Desnoyers et al., "Tumor-Specific Activation of an EGFR-Targeting Probody Enhances Therapeutic Index," Sci. Transl. Med. 5(207):207ra144 (2013) (10 pages).

(56) References Cited

OTHER PUBLICATIONS

Drent et al., "A Rational Strategy for Reducing On-Target Off-Tumor Effects of CD38-Chimeric Antigen Receptors by Affinity Optimization," Molecular Therapy. 25(8): 1946-58 (2017).
Huang et al., "In Vivo Deamidation Characterization of Monoclonal Antibody by LC/MS/MS," Anal. Chem. 77(5): 1432-9 (2005).
Kelley et al., "Thermodynamic Analysis of an Antibody Functional Epitope," Biochemistry. 32(27): 6828-35 (1993).
Kortt et al., "Dimeric and trimeric antibodies: high avidity scFvs for cancer targeting," Biomolecular Engineering. 18:95-108 (2001) (15 pages).
Liu et al., "Affinity-Tuned ErbB2 or EGFR Chimeric Antigen Receptor T Cells Exhibit an Increased Therapeutic Index against Tumors in Mice," Cancer Res. 75(17): 3596-607 (2015) (13 pages).
Liu et al., "Heteroantibody duplexes target cells for lysis by cytotoxic T lymphocytes," Proc Natl Acad Sci U S A. 82(24):8648-52 (1985).
Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).
Saphire et al., "Crystal structure of a neutralizing human IgG against HIV-1: a template for vaccine design," Science. 293(5532):1155-9 (2001).
Spiess et al., "Alternative molecular formats and therapeutic applications for bispecific antibodies," Molecular Immunology. 67:95-106 (2015).
Weidle et al., "The Intriguing Options of Multispecific Antibody Formats for Treatment of Cancer," Cancer Genomics & Proteomics. 10:1-18 (2013) (18 pages).
Wuellner et al., "Bispecific CD3/HER2 Targeting FynomAb Induces Redirected T Cell-Mediated Cytolysis with High Potency and Enhanced Tumor Selectivity," Antibodies. 4(4): 426-440 (2015) (15 pages).
Yan et al., "Succinimide Formation at Asn 55 in the Complementarity Determining Region of a Recombinant Monoclonal Antibody IgG1 Heavy Chain," Biotechnology. 98(10): 3509-21 (2009).
Yang et al., "Improving Trastuzumab's Stability Profile by Removing the Two Degradation Hotspots," Journal of Pharmaceutical Sciences. 104(6): 1960-70 (2015).
Communication pursuant to Rules 161(1) for European Patent Application No. 17808689.8, dated Jun. 27, 2019 (3 pages).
International Preliminary Report on Patentability for International Patent Application No. PCT/US2017/061683 dated May 21, 2019 (7 pages).
Diefenbach et al. "An individualized risk mitigation approach for safety: experience from the mosunetuzumab (CD20/CD3 bispecific antibody) development program in relation to neurotoxicity risk," 61st Ash Annual Meeting & Exposition 10 (2019).
Haile et al. "Soluble CD80 Restores T Cell Activation and Overcomes Tumor Cell Programmed Death L ligand 1-Mediated Immune Suppression," J Immunol. 191:2829-2836 (2013).
Huang et al., "Structual chemistry and therapeutic intervention of protein-protein interactions in immune response, human immunodeficiency virus entry and apoptosis ," Pharmacology & Therapeutics. 86(3):201-215 (2000).
Li et al. "Exposure-response analyses indicate a promising benefit/risk profile of mosunetuzumab in relapsed and refractory non-Hodgkin lymphoma," 61st Ash Annual Meeting & Exposition (2019).
Milne et al. "Systematic Analysis of Immune Infiltrates in High-Grade Serous Ovarian Cancer Reveals CD20, FoxP3 and TIA-1 as Positive Prognostic Factors," PLoS One. 4(7):e6412 (2009).
Paino et al. "Reply to Response to CD20 Positive Cells are Undetectable in the Majority of Multiple Myeloma Cell Lines and are not Associated With a Cancer Stem Cell Phenotype," Haematologica. 97(7):1110-1114 (2012).
Shi et al. "Margin-Infiltrating CD20+ B Cells Display an Atypical Memory Phenotype and Correlate with Favorable Prognosis in Hepatocellular Carcinoma," Clinical Cancer Research. 19(21):5994-6003 (2013).

Somasundaram et al."Will Engineered T Cells Expressing CD20 scFv Eradicate Melanoma?," Mol Ther. 19(4):638-40 (2011).
Stein et al. "Novel and Emerging Drugs for Acute Myeloid Leukemia," Curr Cancer Drug Targets. 12(5):522-530 (2012).
Wells et al. "Reaching for high-hanging fruit in drug discovery at protein-protein interfaces," Nature. 450 (7172):1001-1009(2007).
Communication Pursuant to Article 94(3) EPC for European Patent Application No. 17808689.8, dated Apr. 30, 2020 (8 pages).
Notice of Reasons for Rejection for Japanese Patent Application No. 2017-557140, dated Jun. 23, 2020 (10 pages).
Notice of Reasons for Rejection for Japanese Patent Application No. 2019-044073, dated Jan. 21, 2020 (4 pages).
Office Action for U.S. Appl. No. 16/144,686 , dated Jun. 10, 2020 (13 pages).
Technical Report Notification for Costa Rican Patent Application No. 2016-0000314, dated Feb. 12, 2020 (10 pages).
"Purified Mouse Anti-Human CD3-epsilon Clone SP34," BD Biosciences,<https://www.bdbiosclences.com/us/reagents/research/antibodies-buffers/immunology-reagents/anti-non-human-primate-antibodies/cell-surface-antigens/purified-mouse-anti-human-cd3-sp34/p/556610>, retrieved on Jan. 4, 2021 (4 pages).
Gonzales et al., "Minimizing the Immunogenicity of Antibodies for Clinical Application," Tumour Biol. 26(1):31-43 (Abstract) (2005).
Hosseini et al., "Mitigating the Risk of Cytokine Release Syndrome in a Phase I Trial of CD20/CD3 Bispecific Antibody Mosunetuzumab in NHL: Impact of Translational System Modeling," NPJ Syst Biol Appl. 6(1):28 (2020) (11 pages).
NIH/NCI, "anti-PD-1 fusion protein AMP-224," dated Jul. 7, 2015, accessed Jul. 31, 2019 (1 page).
Sen et al., "Use of anti-CD3x anti-HER2/neu bispecific antibody for redirecting cytotoxicity of activated T cells toward HER2/neu+ tumors," J Hematother Stem Cell Res. 10(2):247-60 (2001).
Wu et al., "Humanization of a Murine Monoclonal Antibody by Simultaneous Optimization of Framework and CDR Residues," J Mol Biol. 294(1):151-162 (1999).
Invitation to Pay Additional Fees for European Patent Application No. 20184006.3, dated Feb. 22, 2021 (2 pages).
Reusch et al., "Anti-CD3 x anti-epidermal growth factor receptor (EGFR) bispecific antibody redirects T-cell cytolytic activity to EGFR-positive cancers in vitro and in an animal model," Clin Cancer Res. 12(1):183-90 (2006) (9 pages).
Wakefield et al., "Addition of a C-terminal extension sequence to transforming growth factor-beta 1 interferes with biosynthetic processing and abolishes biological activity," Growth Factors. 5(3):243-53 (1991).
Gaston et al., "Intracellular delivery of therapeutic antibodies into specific cells using antibody-peptide fusions," Sci Rep. 9(1):18688 (2019) (12 pages).
Lord et al., "Structure-based engineering to restore high affinity binding of an isoform-selective anti-TGFβ1 antibody," MAbs. 10(3):444-452 (2018).
Leabman et al., "Effects of altered FcγR binding on antibody pharmacokinetics in cynomolgus monkeys," MAbs. 5(6):896-903 (2013) (27 pages).
Donaldson et al., "Design and development of masked therapeutic antibodies to limit off-target effects: application to anti-EGFR antibodies," available in PMC Jan. 16, 2013, published in final edited form as: Cancer Biol Ther. 8(22): 2147-52 (2009) (12 pages).
Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," J Transl Med. 11:160 (2013) (9 pages).
Han et al., "Masked Chimeric Antigen Receptor for Tumor-Specific Activation," Mol Ther. 25(1):274-84 (2017).
Polu et al., "Probody therapeutics for targeting antibodies to diseased tissue," Expert Opin Biol Ther. 14(8):1049-53 (2014).
Yang et al., "Generation and characterization of a target-selectively activated antibody against epidermal growth factor receptor with enhanced anti-tumor potency," MAbs. 7(2):440-50 (2015).
Mariuzza et al., "The structural basis of antigen-antibody recognition," Annu Rev Biophys Biophys Chem. 16:139-159 (1987).

(56) References Cited

OTHER PUBLICATIONS

Salmeron et al., "A conformational epitope expressed upon association of CD3-epsilon with either CD3-delta or CD3-gamma is the main target for recognition by anti-CD3 monoclonal antibodies," J Immunol. 147(9): 3047-52 (1991).
Erster et al., "Site-specific targeting of antibody activity in vivo mediated by disease-associated proteases," J Control Release. 161(3): 804-12 (2012).
Desnoyers et al., "Tumor-specific activation of an EGFR-targeting probody enhances therapeutic index," Sci Transl Med. 5(207):207ra144 (2013) (2 pages).
Lu et al., "Tetravalent anti-CD20/CD3 bispecific antibody for the treatment of B cell lymphoma," Biochem Biophys Res Commun. 473(4):808-813 (2016).
First Examination Report for Indian Application No. 201617023207, dated Mar. 26, 2021 (6 pages).
Reusch et al., "Anti-CD3 x anti-epidermal growth factor receptor (EGFR) bispecific antibody redirects T-cell cytolytic activity to EGFR-positive cancers in vitro and in an animal model," Clin Cancer Res. 12(1):183-190 (2006) (9 pages).
Notice of Reasons for Rejection for Japanese Patent Application No. 2019-524370, dated Nov. 9, 2021 (8 pages).
Schuster et al., "Immunotherapy with the trifunctional anti-CD20 x anti-CD3 antibody FBTA05 (Lymphomun) in paediatric high-risk patients with recurrent CD20-positive B cell malignancies," Br J Haematol. 169:90-102 (2015) (14 pages).
Huehls et al., "Bispecific T-cell engagers for cancer immunotherapy," Immunol Cell Biol. 93(3):290-6 (2015).
Office Action for Taiwanese Patent Application No. 106139512, dated Feb. 10, 2022 (13 pages).

\* cited by examiner

DOSING FOR TREATMENT WITH ANTI-CD20/ANTI-CD3 BISPECIFIC ANTIBODIES

FIELD OF THE INVENTION

The present invention relates to the treatment of cancers, such as B cell proliferative disorders. More specifically, the invention concerns the specific treatment of human patients having a B cell proliferative disorder using anti-cluster of differentiation 20 (CD20)/anti-cluster of differentiation 3 (CD3) bispecific antibodies.

BACKGROUND

Cancers are characterized by the uncontrolled growth of cell subpopulations. Cancers are the leading cause of death in the developed world and the second leading cause of death in developing countries, with over 14 million new cancer cases diagnosed and over eight million cancer deaths occurring each year. The National Cancer Institute has estimated that greater than half a million Americans will die of cancer in 2016, accounting for nearly one out of every four deaths in the country. As the elderly population has grown, the incidence of cancer has concurrently risen, as the probability of developing cancer is more than two-fold higher after the age of seventy. Cancer care thus represents a significant and ever-increasing societal burden.

Hematologic cancers, in particular, are the second leading cause of cancer-related deaths. Hematologic cancers include B cell proliferative disorders, such as non-Hodgkin's lymphoma (NHL) (e.g., diffuse-large B cell lymphoma (DLBCL)), which advances quickly and is fatal if untreated. Although treatment with the monoclonal anti-cluster of differentiation 20 (CD20) antibody rituximab has resulted in fewer relapsed DLBCL patients, it has become increasing challenging to treat those patients with relapsed or refractory DLBCL. For such patients, alternative or secondary treatment modalities, such as bispecific antibody-based immunotherapies, may be particularly efficacious. Bispecific antibodies are capable of simultaneously binding cell surface antigens on cytotoxic cells (e.g., T cells, via binding to cluster of differentiation 3 (CD3)) and cancer cells (e.g., B cells, via binding to CD20), with the intent that the bound cytotoxic cell will destroy the bound cancer cell. However, such antibody-based immunotherapies may be limited by unwanted effects, including cytokine-driven toxicities (e.g., cytokine release syndrome (CRS)), infusion-related reactions (IRRs), severe tumor lysis syndrome (TLS), and central nervous system (CNS) toxicities.

Thus, there is an unmet need in the field for the development of efficacious methods of dosing therapeutic bispecific antibodies (e.g., anti-CD20/anti-CD3 bispecific antibodies) for the treatment of cancers (e.g., B cell proliferative disorders) that achieve a more favorable benefit-risk profile.

SUMMARY OF THE INVENTION

The present invention relates to methods of treating a subject having cancer (e.g., a B cell proliferative disorder) using anti-cluster of differentiation 20 (CD20)/anti-cluster of differentiation 3 (CD3) bispecific antibodies.

In one aspect, the invention features a method of treating a subject having a cancer (e.g., a B cell proliferative disorder) comprising administering to the subject a bispecific antibody that binds to CD20 and CD3 in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the CD1 and the C1D2 are each no greater than the C1D3, and (b) the second dosing cycle comprises a single dose (C2D1) of the bispecific antibody, wherein the C2D1 is equal to or greater than the C1D3, wherein the C1D1, the C1D2, and the C1D3 have a cumulative dose that is about 50% greater than a highest cleared dose of the bispecific antibody in a first dosing cycle of a non-fractionated, dose-escalation dosing regimen, and wherein the highest cleared dose is between about 0.2 mg to about 30 mg. In some embodiments, the C1D3 is equal to the highest cleared dose of the bispecific antibody in the first dosing cycle of the non-fractionated, dose-escalation dosing regimen. In some embodiments, the C1D2 and the C1D1 are equal. In some embodiments, the C1D2 is greater than the C1D1 by about 50% to about 250%. In some embodiments, the C1D3 is greater than the C1D2 by about 150% to about 300%.

In another aspect, the invention features a method of treating a subject having a B cell proliferative disorder comprising administering to the subject a bispecific antibody that binds to CD20 and CD3 in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the C1D1 and the C1D2 are each no greater than the C1D3, and wherein the C1D1 is between about 0.0056 mg to about 12.50 mg, the C1D2 is between about 0.0125 mg to about 20.00 mg, and the C1D3 is between about 0.0500 mg to about 50.00 mg; and (b) the second dosing cycle comprises a single dose of the bispecific antibody, wherein the C2D1 is equal to or greater than the C1D3 and is between about 0.0500 mg to about 50.00 mg. In some embodiments, (a) the C1D1 is between about 0.02 mg to about 4.0 mg, the C1D2 is between about 0.05 mg to about 20.0 mg, and the C1D3 is between about 0.2 mg to about 50.0 mg, and (b) the C2D1 is between about 0.2 mg to about 50.0 mg. In some embodiments, (a) the C1D1 is between about 0.4 mg to about 4.0 mg, the C1D2 is between about 1.0 mg to about 20.0 mg, and the C1D3 is between about 3.0 mg to about 50.0 mg, and (b) the C2D1 is between about 3.0 mg to about 50.0 mg. In some embodiments, (a) the C1D1 is between about 0.4 mg to about 4.0 mg, the C1D2 is between about 1.0 mg to about 20.0 mg, and the C1D3 is between about 3.0 mg to about 20.0 mg, and (b) the C2D1 is between about 3.0 mg to about 20.0 mg. In some embodiments, (a) the C1D1 is between about 0.8 mg to about 3.0 mg, the C1D2 is between about 1.0 mg to about 6.0 mg, and the C1D3 is between about 3.0 mg to about 50.0 mg, and (b) the C2D1 is between about 3.0 mg to about 50.0 mg. In some embodiments, (a) the C1D1 is between about 0.8 mg to about 3.0 mg, the C1D2 is between about 1.0 mg to about 6.0 mg, and the C1D3 is between about 3.0 mg to about 20.0 mg, and (b) the C2D1 is between about 3.0 mg to about 20.0 mg. In some embodiments, (a) the C1D1 is about 1.0 mg, the C1D2 is about 2.0 mg, and the C1D3 is between about 3.0 mg to about 50.0 mg (e.g., the C1D3 is about 6.0 mg), and (b) the C2D1 is between about 3.0 mg to about 50.0 mg (e.g., the C2D1 is about 6.0 mg). In some embodiments, (a) the C1D1 is about 1.0 mg, the C1D2 is about 2.0 mg, and the C1D3 is between about 3.0 mg to about 50.0 mg, and (b) the C2D1 is equal to the C1D3. In some embodiments, (a) the C1D1 is about 1.0 mg, the C1D2 is about 2.0 mg, and the C1D3 is about 6.0 mg, and (b) the C2D1 is equal to the C1D3. In some embodiments, (a) the C1D1 is between about 0.02 mg to about 4.0 mg, the C1D2 is between about 0.05 mg to about 20.0 mg, and the C1D3 is between about 0.2 mg to about 20.0 mg, and (b) the C2D1 is between about 3.0 mg to about 20.0 mg. In some embodiments, (a) the C1D1 is between about 0.4 mg to about 4.0 mg, the C1D2 is between about 1.0 mg to about 20.0 mg, and the C1D3 is between about 3.0 mg to about 20.0 mg, and (b) the C2D1 is between about 3.0 mg to about 20.0 mg. In some embodiments, (a) the C1D1 is between about 0.8 mg to about 3.0 mg, the C1D2 is between about 1.0 mg to about 6.0 mg, and the C1D3 is between about 3.0 mg to about 20.0 mg, and (b) the C2D1 is between about 3.0 mg to about 20.0 mg. In some embodiments, (a) the C1D1 is between about 0.8 mg to about 3.0 mg, the C1D2 is between about 1.0 mg to about 6.0 mg, and the C1D3 is between about 3.0 mg to about 6.0 mg, and (b) the C2D1 is between about 3.0 mg to about 6.0 mg.

In some embodiments, (a) the C1D1 is about 0.8 mg, the C1D2 is about 2.0 mg, and the C1D3 is about 4.2 mg, and (b) the C2D1 is about 4.2 mg. In some embodiments, (a) the C1D1 is about 1.0 mg, the C1D2 is about 1.0 mg, and the C1D3 is about 3.0 mg, and (b) the C2D1 is about 3.0 mg. In some embodiments, (a) the C1D1 is about 1.0 mg, the C1D2 is about 2.0 mg, and the C1D3 is about 6.0 mg, and (b) the C2D1 is about 6.0 mg. In some embodiments, (a) the C1D1 is about 0.8 mg, the C1D2 is about 2.0 mg, and the C1D3 is about 6.0 mg, and (b) the C2D1 is about 6.0 mg. In some embodiments of any of the above aspects, the length of the first dosing cycle is 21 days. In some embodiments, the method comprises administering to the subject the C1D1, the C1D2, and the C1D3 on or about Days 1, 8, and 15, respectively, of the first dosing cycle.

In some embodiments of any of the above aspects, the length of the second dosing cycle is 21 days. In some embodiments, the method comprises administering to the subject the C2D1 on Day 1 of the second dosing cycle.

In some embodiments of any of the above aspects, the dosing regimen comprises one or more additional dosing cycles. In some embodiments, the dosing regimen comprises 1 to 14 additional dosing cycles. In some embodiments, the dosing regimen comprises one to six additional dosing cycles. In some embodiments, the length of each of the one or more additional dosing cycles is 7 days, 14 days, 21 days, or 28 days. In some embodiments, the length of each of the one or more additional dosing cycles is 21 days. In some embodiments, each of the one or more additional dosing cycles comprises a single dose of the bispecific antibody. In some embodiments, the method comprises administering to the subject the single dose of the one or more additional dosing cycles on Day 1 of the one or more additional dosing cycles.

In some embodiments of any of the above aspects, the bispecific antibody comprises an anti-CD20 arm comprising a first binding domain comprising the following six hypervariable regions (HVRs): (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSN-SYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some embodiments, the bispecific antibody comprises an anti-CD20 arm comprising a first binding domain comprising (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b). In some embodiments, the first binding domain comprises a VH domain comprising an amino acid sequence of SEQ ID NO: 7 and a VL domain comprising an amino acid sequence of SEQ ID NO: 8. In some embodiments, the bispecific antibody comprises an anti-CD3 arm comprising a second binding domain comprising the following six HVRs: (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYS-NYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (1 an HVR-L3 comprising the amino acid sequence of TQSFILRT (SEQ ID NO: 14). In some embodiments, the bispecific antibody comprises an anti-CD3 arm comprising a second binding domain comprising (a) a VH domain comprising an amino acid sequence having at least 95% sequence identity to the amino acid sequence of SEQ ID NO: 15; (b) a VL domain comprising an amino acid sequence having at least 95% sequence identity to the amino acid sequence of SEQ ID NO: 16; or (c) a VH domain as in (a) and a VL domain as in (b). In some embodiments, the second binding domain comprises a VH domain comprising an amino acid sequence of SEQ ID NO: 15 and a VL domain comprising an amino acid sequence of SEQ ID NO: 16.

In some embodiments of any of the above aspects, the bispecific antibody comprises an aglycosylation site mutation. In some embodiments, the aglycosylation site mutation reduces effector function of the bispecific antibody. In some embodiments, the aglycosylation site mutation is a substitution mutation. In some embodiments, the bispecific antibody comprises a substitution mutation in the Fc region that reduces effector function. In some embodiments, the substitution mutation is at amino acid residue N297, L234, L235, and/or D265 (EU numbering). In some embodiments, the substitution mutation is selected from the group consisting of N297G, N297A, L234A, L235A, D265A, and P329G. In some embodiments, the substitution mutation is at amino acid residue N297. In some embodiments, the substitution mutation is N297A.

In some embodiments of any of the above aspects, the bispecific antibody is a monoclonal antibody. In some embodiments of any of the above aspects, the bispecific antibody is a humanized antibody. In some embodiments of any of the above aspects, the bispecific antibody is a chimeric antibody. In some embodiments of any of the above aspects, the bispecific antibody is an antibody fragment that binds CD20 and CD3. In some embodiments, the antibody fragment is selected from the group consisting of Fab, Fab'-SH, Fv, scFv, and (Fab')$_2$ fragments. In some embodiments of any of the above aspects, the bispecific antibody is a full-length antibody. In some embodiments of any of the above aspects, the bispecific antibody is an IgG antibody. In some embodiments, the IgG antibody is an IgG$_1$ antibody.

In some embodiments of any of the above aspects, the bispecific antibody comprises one or more heavy chain constant domains, wherein the one or more heavy chain constant domains are selected from a first CH1 (CH1$_1$) domain, a first CH2 (CH2$_1$) domain, a first CH3 (CH3$_1$)

domain, a second CH1 (CH1$_2$) domain, second CH2 (CH2$_2$) domain, and a second CH3 (CH3$_2$) domain. In some embodiments, at least one of the one or more heavy chain constant domains is paired with another heavy chain constant domain. In some embodiments, the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain. In some embodiments, the CH3$_1$ and CH3$_2$ domains meet at an interface between the protuberance and cavity. In some embodiments, the CH2, and CH2$_2$ domains each comprise a protuberance or cavity, and wherein the protuberance or cavity in the CH2$_1$ domain is positionable in the cavity or protuberance, respectively, in the CH2$_2$ domain. In some embodiments, the CH2$_1$ and CH2$_2$ domains meet at an interface between said protuberance and cavity.

In some embodiments of any of the above aspects, the bispecific antibody is administered to the subject as a monotherapy.

In other embodiments of any of the above aspects, the bispecific antibody is administered to the subject as a combination therapy. In some embodiments, the bispecific antibody is administered to the subject concurrently with an additional therapeutic agent (e.g., atezolizumab). In other embodiments, the bispecific antibody is administered to the subject prior to the administration of an additional therapeutic agent (e.g., atezolizumab). In some embodiments, the additional therapeutic agent is atezolizumab. In some embodiments, the method further comprises administering to the subject a first dose of atezolizumab concurrently with the C2D1 of the bispecific antibody on Day 1 of the second dosing cycle. In some embodiments, the method further comprises administering to the subject atezolizumab concurrently with the single dose of the bispecific antibody of the one or more additional dosing cycles on Day 1 of the one or more additional dosing cycles. In some embodiments, atezolizumab is only administered to the subject concurrently with the bispecific antibody. In some embodiments, each dose of atezolizumab is about 1200 mg.

In yet other embodiments, the bispecific antibody is administered to the subject subsequent to the administration of an additional therapeutic agent (e.g., obinutuzumab (GAZYVA®) or tocilizumab (ACTEMRA®/RoACTEMRA®)).

In some embodiments of any of the above aspects, the B cell proliferative disorder is a non-Hodgkin's lymphoma (NHL) or a chronic lymphoid leukemia (CLL). In some embodiments, the NHL is a diffuse-large B cell lymphoma (DLBCL). In some embodiments, the DLBCL is a relapsed or refractory DLBCL. In some embodiments, the NHL is a follicular lymphoma (FL). In some embodiments, the NHL is a primary mediastinal (thymic) large B cell lymphoma (PMLBCL).

In some embodiments of any of the above aspects, the administering is by intravenous infusion.

In some embodiments of any of the above aspects, the administering is administering subcutaneously.

In some embodiments of any one the above aspects, the subject experiences a cytokine release syndrome (CRS) event, and the method further comprises administering to the subject an effective amount of an interleukin-6 receptor (IL-6R) antagonist (e.g., an anti-IL-6R antibody, e.g., tocilizumab (ACTEMRA®/RoACTEMRA®)) to manage the CRS event.

In some embodiments, tocilizumab is administered intravenously to the subject as a single dose of about 8 mg/kg.

In other embodiments, the CRS event does not resolve or worsens within 24 hours of treating the symptoms of the CRS event, and the method further comprises administering to the subject one or more additional doses of the IL-6R antagonist (e.g., an anti-IL-6R antibody, e.g., tocilizumab) to manage the CRS event. In some embodiments, the CRS event does not resolve or worsens within 24 hours of treating the symptoms of the CRS event, and the method further comprises administering to the subject one or more additional doses of tocilizumab to manage CRS event. In some embodiments, the one or more additional doses of tocilizumab is administered intravenously to the subject at a dose of about 8 mg/kg. In some embodiments, the method further comprises administering to the subject an effective amount of a corticosteroid. In some embodiments, the corticosteroid is administered intravenously to the subject. In some embodiments, the corticosteroid is methylprednisolone. In some embodiments, the methylprednisolone is administered at a dose of about 2 mg/kg per day. In other embodiments, the corticosteroid is dexamethasone. In some embodiments, the dexamethasone is administered at a dose of about 10 mg.

DETAILED DESCRIPTION OF EMBODIMENTS OF THE INVENTION

I. Definitions

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

The terms "anti-CD20/anti-CD3 antibody" and "antibody that binds to CD20 and CD3," or variants thereof, refer to a multispecific antibody (e.g., a bispecific antibody) that is capable of binding to CD20 and CD3 with sufficient affinity such that the antibody is useful as a diagnostic and/or therapeutic agent in targeting CD20 and/or CD3. In one embodiment, the extent of binding of an anti-CD20/anti-CD3 antibody to an unrelated, non-CD3 protein and/or non-CD20 protein is less than about 10% of the binding of the antibody to CD3 and/or CD20 as measured, e.g., by a radioimmunoassay (RIA). In certain embodiments, an antibody that binds to CD20 and CD3 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-CD20/anti-CD3 antibody binds to an epitope of CD3 that is conserved among CD3 from different species and/or an epitope of CD20 that is conserved among CD20 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'$_2$, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); famesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.cndot.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

The term "chimeric" antibody refers to an antibody in which a portion of the heavy and/or light chain is derived from a particular source or species, while the remainder of the heavy and/or light chain is derived from a different source or species.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The term "cluster of differentiation 20" or "CD20," as used herein, refers to any native CD20 from any vertebrate source, including mammals such as primates (e.g. humans) and rodents (e.g., mice and rats), unless otherwise indicated. The term encompasses "full-length," unprocessed CD20, as well as any form of CD20 that results from processing in the cell. The term also encompasses naturally occurring variants of CD20, including, for example, splice variants or allelic variants. CD20 includes, for example, human CD20 protein (see, e.g., NCBI RefSeq Nos. NP_068769.2 and NP_690605.1), which is 297 amino acids in length and may be generated, for example, from variant mRNA transcripts that lack a portion of the 5' UTR (see, e.g., NCBI RefSeq No. NM_021950.3) or longer variant mRNA transcripts (see, e.g., NCBI RefSeq No. NM_152866.2).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

It is understood that aspects and embodiments of the invention described herein include "comprising," "consisting," and "consisting essentially of" aspects and embodiments.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In another embodiment, the cell proliferative disorder is a tumor.

The terms "B cell proliferative disorder" or "B cell malignancy" refer to disorders that are associated with some degree of abnormal B cell proliferation and include, for example, lymphomas, leukemias, myelomas, and myelodysplastic syndromes. In one embodiment, the B cell proliferative disorder is a lymphoma, such as non-Hodgkin's lymphoma (NHL), including, for example, diffuse large B cell lymphoma (DLBCL) (e.g., relapsed or refractory DLBCL). In another embodiment, the B cell proliferative disorder is a leukemia, such as chronic lymphocytic leukemia (CLL).

The terms "cancer" and "cancerous" refer to or describe the physiological condition in mammals that is typically characterized by unregulated cell growth. Examples of cancer include, but are not limited to, hematologic cancers, such as mature B cell cancers, excluding Hodgkin's lymphoma, but including non-Hodgkin's lymphoma (NHL), such as diffuse large B cell lymphoma (DLBCL), which may be relapsed or refractory DLBCL. Other specific examples of cancer also include germinal-center B cell-like (GCB) diffuse large B cell lymphoma (DLBCL), activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, Waldenstrom macroglobulinemia, heavy chain diseases, a heavy chain disease, γ heavy chain disease, p heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cellihistiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, primary mediastinal (thymic) large B cell lymphoma (PMLBCL), intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and Burkitt lymphoma, and B cell lymphoma, unclassifiable, with features intermediate between DLBCL and classical Hodgkin's lymphoma. Further examples of cancer include, but are not limited to, carcinoma, lymphoma, blastoma, sarcoma, and leukemia or lymphoid malignancies, including B cell lymphomas. More particular examples of such cancers include, but are not limited to, multiple myeloma (MM); low grade/follicular NHL; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; AIDS-related lymphoma; and acute lymphoblastic leukemia (ALL); chronic myeloblastic leukemia; and post-transplant lymphoproliferative disorder (PTLD).

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder," and "tumor" are not mutually exclusive as referred to herein.

The term "tumor antigen," as used herein, may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are tumor antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. In one aspect the tumor antigen is CD20.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of a compound, for example, an anti-CD20/anti-CD3 antibody or a composition (e.g., pharmaceutical composition) thereof, is at least the minimum amount required to achieve the desired therapeutic or prophylactic result, such as a measurable improvement or prevention of a particular disorder (e.g., a cancer, e.g., a B cell proliferative disorder, e.g., NHL, e.g., DLBCL). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis: inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H12), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallurn et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject or individual is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N-to C-terminus, each heavy chain has a variable region (VH), also called a variable heavy domain or a heavy chain variable domain, followed by three constant domains (CH1, CH2, and CF-3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The term "protein," as used herein, refers to any native protein from any vertebrate source, including mammals such as primates (e.g. humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof, such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a B cell proliferative disorder, e.g., NHL, e.g., DLBCL). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the reduction or inhibition of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the fractionated, dose-escalation dosing regimen of the invention relative to treatment with an anti-CD20/anti-CD3 bispecific antibody using an non-fractioned dosing regimen. In other embodiments, reduce or inhibit can refer to effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis, with a result being to restore or enhance T-cell function (e.g., proliferation, cytokine production, target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates, or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen-binding fragments thereof, immunoadhesins, fusion proteins, oligopeptides, and other molecules that decrease, block, inhibit, abrogate, or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific embodiment, a PD-1 binding antagonist is MDX-1106 (nivolumab), described herein. In another specific embodiment, a PD-1 binding antagonist is MK-3475 (lambrolizumab), described herein. In another specific embodiment, a PD-1 binding antagonist is CT-011 (pidilizumab), described herein. In another specific embodiment, a PD-1 binding antagonist is AMP-224, described herein.

The term "PD-L1 binding antagonist" refers to a molecule that decreases, blocks, inhibits, abrogates, or interferes with signal transduction resulting from the interaction of PD-L1 with either one or more of its binding partners, such as PD-1 or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or 87-1. In some embodiments, the PD-L1 binding antagonists include anti-PD-L1 antibodies, antigen-binding fragments thereof, immunoadhesins, fusion proteins, oligopeptides, and other molecules that decrease, block, inhibit, abrogate, or interfere with signal transduction resulting from the interaction of PD-L1 with one or more of its binding partners, such as PD-1 or B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific embodiment, the anti-PD-L1 antibody is atezolizumab (CAS Registry Number: 1422185-06-5), also known as MPDL3280A, and described herein. In another specific embodiment, the anti-PD-L1 antibody is YW243.55.S70, described herein. In another specific embodiment, the anti-PD-L1 antibody is MDX-1105, described herein. In still another specific aspect, the anti-PD-L1 antibody is MEDI4736, described herein.

The term "PD-L2 binding antagonist" refers to a molecule that decreases, blocks, inhibits, abrogates, or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen-binding fragments thereof, immunoadhesins, fusion proteins, oligopeptides, and other molecules that decrease, block, inhibit, abrogate, or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

As used herein, a "week" is 7 days±2 days.

As used herein, "administering" is meant a method of giving a dosage of a compound (e.g., an anti-CD20/anti-CD3 antibody) or a composition (e.g., a pharmaceutical composition, e.g., a pharmaceutical composition including an anti-CD20/anti-CD3 antibody) to a subject. The compounds and/or compositions utilized in the methods described herein can be administered, for example, intravenously (e.g., by intravenous infusion), subcutaneously, intramuscularly, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subconjunctivally, intravesicularily, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

II. Therapeutic Methods

The invention is based, in part, on methods of treating a subject having cancer (e.g., a B cell proliferative disorder) using fractionated, dose-escalation dosing regimens with anti-cluster of differentiation 20 (CD20)/anti-cluster of differentiation 3 (CD3) bispecific antibodies. The methods are expected to reduce or inhibit unwanted treatment effects, which include cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities. Therefore, the methods are useful for treating the subject while achieving a more favorable benefit-risk profile.

The invention provides methods useful for treating a subject having cancer (e.g., a B cell proliferative disorder, e.g., non-Hodgkin's lymphoma (NHL), e.g., diffuse large B-cell lymphoma (DLBCL) (e.g., relapsed or refractory DLBCL), follicular lymphoma (FL), or primary mediastinal (thymic) large B cell lymphoma (PMLBCL)) that include administering to the subject a bispecific antibody that binds to CD20 and CD3 (i.e., an anti-CD20/anti-CD3 antibody) in a fractionated, dose-escalation dosing regimen.

The invention provides a method of treating a subject having a cancer (e.g., a B cell proliferative disorder) comprising administering to the subject a bispecific antibody that binds to CD20 and CD3 in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the C1D1 and the C1D2 are each no greater than the C1D3, and (b) the second dosing cycle comprises a single dose (C2D1) of the bispecific antibody, wherein the C2D1 is equal to or greater than the C1D3, wherein the C1D1, the C1D2, and the C1D3 have a cumulative dose that is about 50% greater than a highest cleared dose (i.e., dose which does not induce unacceptable toxicity in a patient) of the bispecific antibody in a first dosing cycle of a non-fractionated, dose-escalation dosing regimen, and wherein the highest cleared dose is between about 0.05 mg to about 30 mg (e.g., between about 0.05 mg to about 25 mg, e.g., between about 0.05 mg to about 20 mg, e.g., between about 0.05 mg to about 15 mg, e.g., between about 0.05 mg to about 13 mg, e.g., between about 0.1 mg to about 13 mg, e.g., between about 0.2 mg to about 13 mg, e.g., between about 0.2 mg to about 10 mg, e.g., between about 0.2 mg to about 7.5 mg, e.g., between about 0.4 mg to about 7.5 mg, e.g., between about 0.4 mg to about 6 mg, e.g., between about 0.4 mg to about 5 mg, e.g., between about 0.8 mg to about 5 mg, e.g., between about 1 mg to about 5 mg, e.g., about 2.8 mg). In some embodiments, the C1D3 is equal to the highest cleared dose of the bispecific antibody in the first dosing cycle of the non-fractionated, dose-escalation dosing regimen. In some embodiments, the C1D2 and the C1D1 are equal. In some embodiments, the C1D2 is greater than the C1D1 by about 50% to about 250% (e.g., the C1D2 is greater than the C1D1 by about 50% to about 225%, e.g., the C1D2 is greater than the C1D1 by about 50% to about 200%, e.g., the C1D2 is greater than the C1D1 by about 50% to about 175%, e.g., the C1D2 is greater than the C1D1 by about 50% to about 150%, e.g., the C1D2 is greater than the C1D1 by about 50% to about 125%, e.g., the C1D2 is greater than the C1D1 by about 50% to about 100%, e.g., the C1D2 is greater than the C1D1 by about 50% to about 75%). In some embodiments, the C1D3 is greater than the C1D2 by about 150% to about 300% (e.g., the C1D3 is greater than the C1D2 by about 150% to about 275%, e.g., the C1D3 is greater than the C1D2 by about 150% to about 250%, e.g., the C1D3 is greater than the C1D2 by about 150% to about 233%, e.g., the C1D3 is greater than the C1D2 by about 150% to about 225%, e.g., the C1D3 is greater than the C1D2 by about 150% to about 200%, e.g., the C1D3 is greater than the C1D2 by about 150% to about 180%, e.g., the C1D3 is greater than the C1D2 by about 150% to about 175%, e.g., the C1D3 is greater than the C1D2 by about 150% to about 167%, e.g., the C1D3 is greater than the C1D2 by about 150% to about 157%).

The invention also provides a method of treating a subject having a cancer (e.g., a B cell proliferative disorder) comprising administering to the subject a bispecific antibody that binds to CD20 and CD3 in a dosing regimen comprising at least a first dosing cycle and a second dosing cycle, wherein: (a) the first dosing cycle comprises a first dose (C1D1), a second dose (C1D2), and a third dose (C1D3) of the bispecific antibody, wherein the C1D1 and the C1D2 are each no greater than the C1D3, and wherein the C1D1 is between about 0.0056 mg to about 12.50 mg (e.g., between about 0.0075 mg to about 12.50 mg, e.g., between about 0.0075 mg to about 12 mg, e.g., between about 0.0075 mg to about 10 mg, e.g., between about 0.0075 mg to about 8 mg, e.g., between about 0.010 mg to about 8 mg, e.g., between about 0.010 mg to about 7 mg, e.g., between about 0.010 mg to about 6 mg, e.g., between about 0.010 mg to about 5 mg, e.g., between about 0.010 mg to about 4 mg, e.g., between about 0.010 mg to about 3.5 mg, e.g., between about 0.015 mg to about 3.5 mg, e.g., between about 0.020 mg to about 3.5 mg, e.g., between about 0.020 mg to about 3.2 mg, e.g., about 0.8 mg or about 1 mg), the C1D2 is between about 0.0125 mg to about 20.00 mg (e.g., between about 0.0125 mg to about 17.5 mg, e.g., between about 0.0125 mg to about 15 mg, e.g., between about 0.020 mg to about 15 mg, e.g., between about 0.025 mg to about 15 mg, e.g., between about 0.030 mg to about 15 mg, e.g., between about 0.035 mg to about 15 mg, e.g., between about 0.040 mg to about 15 mg, e.g., between about 0.045 mg to about 15 mg, e.g., between about 0.050 mg to about 15 mg, e.g., between about 0.050 mg to about 12.5 mg, e.g., between about 0.050 mg to about 10 mg, e.g., between about 0.050 mg to about 7.5 mg, e.g., between about 0.050 mg to about 5 mg, e.g., about 1 mg or about 2 mg), and the C1D3 is between about 0.0500 mg to about 50 mg (e.g., between about 0.055 mg to about 50 mg, e.g., between about 0.10 mg to about 50 mg, e.g., between about 1.0 mg to about 50 mg, e.g., between about 2 mg to about 10 mg, e.g., between about 3.0 mg to about 6.0, e.g., about 3.0 mg, 4.2 mg, or 6 mg); and (b) the second dosing cycle comprises a single dose (C2D1) of the bispecific antibody, wherein the C2D1 is equal to or greater than the C1D3 and is between about 0.0500 mg to about 50 mg (e.g., 0.0500 mg to about 50 mg (e.g., between about 0.055 mg to about 50 mg, e.g., between about 0.10 mg to about 50 mg, e.g., between about 1.0 mg to about 50 mg, e.g., between about 1.0 mg to about 35 mg, e.g., between about 2 mg to about 10 mg, e.g., between about 3.0 mg to about 6.0 mg, e.g., about 3.0 mg, 4.2, mg or 6 mg). In some instances, for example, (a) the C1D1 is between about 0.02 mg to about 4.0 mg, the C1D2 is between about 0.05 mg to about 20.0 mg, and the C1D3 is between about 0.2 mg to about 50.0 mg, and (b) the C2D1 is between about 3.0 mg to about 50.0 mg. In some instances, (a) the C1D1 is between about 0.4 mg to about 4.0 mg, the C1D2 is between about 1.0 mg to about 20.0 mg, and the C1D3 is between about 3.0 mg to about 50.0 mg, and (b) the C2D1 is between about 3.0 mg to about 50.0 mg. In some instances, (a) the C1D1 is between about 1.0 mg to about 3.0 mg, the C1D2 is between about 2.0 mg to about 6.0 mg, and the C1D3 is between about 6.0 mg to about 50.0 mg, and (b) the C2D1 is between about 6.0 mg to about 50.0 mg. In some instances, (a) the C1D1 is about 1.0 mg, the C1D2 is about 2.0 mg, and the C1D3 is between about 6.0 mg to about 50.0 mg, and (b) the C2D1 is between about 6.0 mg to about 50.0 mg. In some instances, (a) the C1D1 is about 1.0 mg, the C1D2 is about 2.0 mg, and the C1D3 is between about 6.0 mg to about 50.0 mg, and (b) the C2D1 is equal to the C1D3. In some instances, (a) the C1D1 is about 1.0 mg, the C1D2 is about 2.0 mg, and the C1D3 is about 20.0 mg, and (b) the C2D1 is equal to the C1D3. In some instances, for example, (a) the C1D1 is between about 0.02 mg to about 4.0 mg, the C1D2 is between about 0.05 mg to about 20.0 mg, and the C1D3 is between about 0.2 mg to about 20.0 mg, and (b) the C2D1 is between about 0.2 mg to about 20.0 mg. In some instances, (a) the C1D1 is between about 0.4 mg to about 4.0 mg, the C1D2 is between about 1.0 mg to about 20.0 mg, and the C1D3 is between about 3.0 mg to about 20.0 mg, and (b) the C2D1 is between about 3.0 mg to about 20.0 mg. In other instances, (a) the C1D1 is between about 0.8 mg to about 3.0 mg, the C1D2 is between about 1.0 mg to about 6.0 mg, and the C1D3 is about 3.0 mg to about 20.0 mg, and (b) the C2D1 is about 3.0 mg to about 20.0 mg. In other instances, (a) the C1D1 is between about 0.8 mg to about 3.0 mg, the C1D2 is between about 1.0 mg to about 6.0 mg, and the C1D3 is about 3.0 mg to about 6.0 mg, and (b) the C2D1 is about 3.0 mg to about 6.0 mg.

In some embodiments, (a) the CD1 is about 0.8 mg, the C1D2 is about 2.0 mg, and the C1D3 is about 4.2 mg, and (b) the C2D1 is about 4.2 mg. In some embodiments, (a) the C1D1 is about 1.0 mg, the C1D2 is about 1.0 mg, and the C1D3 is about 3.0 mg, and (b) the C2D1 is about 3.0 mg. In some embodiments, (a) the C1D1 is about 1.0 mg, the C1D2 is about 2.0 mg, and the C1D3 is about 6.0 mg, and (b) the C2D1 is about 6.0 mg. In some embodiments, (a) the C1D1 is about 0.8 mg, the C1D2 is about 2.0 mg, and the C1D3 is about 6.0 mg, and (b) the C2D1 is about 6.0 mg. The invention also provides a method of treating a subject having a cancer (e.g., a B cell proliferative disorder) comprising administering to the subject a bispecific antibody that binds to CD20 and CD3 in a dosing regimen comprising a first dosing cycle and, optionally, a second dosing cycle, wherein: (a) the first dosing cycle comprises a first dose (C1D1) and a second dose (C1D2) of the bispecific antibody, wherein the C1D1 is no greater than the C1D2 dose, and optionally (b) the second dosing cycle comprises a single dose (C2D1) of the bispecific antibody, wherein the C2D1 is equal to or greater than the C1D2, wherein the C1D1 and the C1D2 have a cumulative dose that is about 50% greater than a highest cleared dose of the bispecific antibody in a first dosing cycle of a non-fractionated, dose-escalation dosing regimen, and wherein the highest cleared dose is between about 0.05 mg to about 30 mg (e.g., between about 0.05 mg to about 25 mg, e.g., between about 0.05 mg to about 20 mg, e.g., between about 0.05 mg to about 15 mg, e.g., between about 0.05 mg to about 13 mg, e.g., between about 0.1 mg to about 13 mg, e.g., between about 0.2 mg to about 13 mg, e.g., between about 0.2 mg to about 10 mg, e.g., between about 0.2 mg to about 7.5 mg, e.g., between about 0.4 mg to about 7.5 mg, e.g., between about 0.4 mg to about 6 mg, e.g., between about 0.4 mg to about 5 mg, e.g., between about 0.8 mg to about 5 mg, e.g., between about 1 mg to about 5 mg, e.g., about 2.8 mg). In some embodiments, the C1D2 is equal to the highest cleared dose of the bispecific antibody in the first dosing cycle of the non-fractionated, dose-escalation dosing regimen. In some instances, the C1D2 is greater than the C1D1 by about 50% to about 250% (e.g., the C1D2 is greater than the C1D1 by about 50% to about 225%, e.g., the C1D2 is greater than the C1D1 by about 50% to about 200%, e.g., the C1D2 is greater than the C1D1 by about 50% to about 175%, e.g., the C1D2 is greater than the C1D1 by about 50% to about 150%, e.g., the C1D2 is greater than the C1D1 by about 50% to about 125%, e.g., the C1D2 is greater than the C1D1 by about 50% to about 100%, e.g., the C1D2 is greater than the C1D1 by about 50% to about 75%).

In some instances, the C1D1 is between about 0.0056 mg to about 12.50 mg (e.g., between about 0.0075 mg to about 12.50 mg, e.g., between about 0.0075 mg to about 12 mg, e.g., between about 0.0075 mg to about 10 mg, e.g., between about 0.0075 mg to about 8 mg, e.g., between about 0.010 mg to about 8 mg, e.g., between about 0.010 mg to about 7 mg, e.g., between about 0.010 mg to about 6 mg, e.g., between about 0.010 mg to about 5 mg, e.g., between about 0.010 mg to about 4 mg, e.g., between about 0.010 mg to about 3.5 mg, e.g., between about 0.015 mg to about 3.5 mg, e.g., between about 0.020 mg to about 3.5 mg, e.g., between about 0.020 mg to about 3.2 mg, e.g., about 0.8 mg or about 1 mg). In some instances, the C1D2 is between about 0.0125 mg to about 19.44 mg (e.g., between about 0.0125 mg to about 17.5 mg, e.g., between about 0.0125 mg to about 15 mg, e.g., between about 0.020 mg to about 15 mg, e.g., between about 0.025 mg to about 15 mg, e.g., between about 0.030 mg to about 15 mg, e.g., between about 0.035 mg to about 15 mg, e.g., between about 0.040 mg to about 15 mg, e.g., between about 0.045 mg to about 15 mg, e.g., between about 0.050 mg to about 15 mg, e.g., between about 0.050 mg to about 12.5 mg, e.g., between about 0.050 mg to about 10 mg, e.g., between about 0.050 mg to about 7.5 mg, e.g., between about 0.050 mg to about 5 mg). In some instances, the C1D2 is between about 0.0500 mg to about 50 mg (e.g., between about 0.055 mg to about 50 mg, e.g., between about 0.055 mg to about 45 mg, e.g., between about 0.055 mg to about 40 mg, e.g., between about 0.055 mg to about 35 mg, e.g., between about 0.055 mg to about 30 mg, e.g., between about 0.10 mg to about 30 mg, e.g., between about 0.15 mg to about 30 mg, e.g., between about 0.15 mg to about 25 mg, e.g., between about 0.15 mg to about 20 mg, e.g., between about 0.15 mg to about 17.5 mg, e.g., between about 0.15 mg to about 15 mg, e.g., between about 0.20 mg to about 15 mg, e.g., between about 0.20 mg to about 12.8 mg, e.g., between about 0.20 mg to about 12.5 mg).

In some instances, the C1D1 is between about 0.0056 mg to about 12.50 mg (e.g., between about 0.0075 mg to about 12.50 mg, e.g., between about 0.0075 mg to about 12 mg, e.g., between about 0.0075 mg to about 10 mg, e.g., between about 0.0075 mg to about 8 mg, e.g., between about 0.010 mg to about 8 mg, e.g., between about 0.010 mg to about 7 mg, e.g., between about 0.010 mg to about 6 mg, e.g., between about 0.010 mg to about 5 mg, e.g., between about 0.010 mg to about 4 mg, e.g., between about 0.010 mg to about 3.5 mg, e.g., between about 0.015 mg to about 3.5 mg, e.g., between about 0.020 mg to about 3.5 mg, e.g., between about 0.020 mg to about 3.2 mg, e.g., about 1.6 mg) and the C1D2 is between about 0.0125 mg to about 19.44 mg (e.g., between about 0.0125 mg to about 17.5 mg, e.g., between about 0.0125 mg to about 15 mg, e.g., between about 0.020 mg to about 15 mg, e.g., between about 0.025 mg to about 15 mg, e.g., between about 0.030 mg to about 15 mg, e.g., between about 0.035 mg to about 15 mg, e.g., between about 0.040 mg to about 15 mg, e.g., between about 0.045 mg to about 15 mg, e.g., between about 0.050 mg to about 15 mg, e.g., between about 0.050 mg to about 12.5 mg, e.g., between about 0.050 mg to about 10 mg, e.g., between about 0.050 mg to about 7.5 mg, e.g., between about 0.050 mg to about 5 mg). In some instances, the C1D1 is between about 0.0056 mg to about 12.50 mg (e.g., between about 0.0075 mg to about 12.50 mg, e.g., between about 0.0075 mg to about 12 mg, e.g., between about 0.0075 mg to about 10 mg, e.g., between about 0.0075 mg to about 8 mg, e.g., between about 0.010 mg to about 8 mg, e.g., between about 0.010 mg to about 7 mg, e.g., between about 0.010 mg to about 6 mg, e.g., between about 0.010 mg to about 5 mg, e.g., between about 0.010 mg to about 4 mg, e.g., between about 0.010 mg to about 3.5 mg, e.g., between about 0.015 mg to about 3.5 mg, e.g., between about 0.020 mg to about 3.5 mg, e.g., between about 0.020 mg to about 3.2 mg, e.g., about 1.6 mg) and the C1D2 is between about 0.0500 mg to about 50 mg (e.g., between about 0.055 mg to about 50 mg, e.g., between about 0.055 mg to about 45 mg, e.g., between about 0.055 mg to about 40 mg, e.g., between about 0.055 mg to about 35 mg, e.g., between about 0.055 mg to about 30 mg, e.g., between about 0.10 mg to about 30 mg, e.g., between about 0.15 mg to about 30 mg, e.g., between about 0.15 mg to about 25 mg, e.g., between about 0.15 mg to about 20 mg, e.g., between about 0.15 mg to about 17.5 mg, e.g., between about 0.15 mg to about 15 mg, e.g., between about 0.20 mg to about 15 mg, e.g., between about 0.20 mg to about 12.8 mg, e.g., between about 0.20 mg to about 12.5 mg). In any of the above instances, the dosing regimen may comprise a first dosing cycle and, optionally, a second dosing cycle, wherein: (a) the first dosing cycle consists of a C1D1 and a C1D2 of the bispecific antibody, and optionally (b) the second dosing cycle comprises a C2D1 of the bispecific antibody. In any of the above instances, the dosing regimen may comprise at least a first dosing cycle and a second dosing cycle, wherein: (a) the first dosing cycle consists of a C1D1 and a C1D2 of the bispecific antibody, and (b) the second dosing cycle consists of a C2D1 of the bispecific antibody.

In some instances, the methods described above may include a first dosing cycle of three weeks or 21 days. In some instances, the methods may include administering to the subject the C1D1, the C1D2, and the C1D3 on or about Days 1, 8, and 15, respectively, of the first dosing cycle.

In some instances, the methods described above may include a second dosing cycle of three weeks or 21 days. In some instances, the methods may include administering to the subject the C2D1 on or about Day 1 of the second dosing cycle.

In some instances, the methods described above may include one or more additional dosing cycles. In some instances, the dosing regimen comprises 1 to 14 additional dosing cycles (e.g., 1, 2, 3, 4, 5, 6, 7, 8, 9, 10, 11, 12, 13, or 14 additional dosing cycles (i.e., the dosing regimen includes one or more of additional dosing cycle(s) C3, C4, C5, C6, C7, C8, C9, C10, C11, C12, C13, C14, C15, and C16). In some instances, the dosing regimen comprises one to six additional dosing cycles (i.e., the dosing regimen includes one or more of additional dosing cycle(s) C3, C4, C5, C6, C7, and C8). In some embodiments, the length of each of the one or more additional dosing cycles is 7 days, 14 days, 21 days, or 28 days. In some instances, the length of each of the one or more additional dosing cycles is three weeks or 21 days. In some instances, each of the one or more additional dosing cycles comprises a single dose of the bispecific antibody. In some instances, the method comprises administering to the subject the single dose of the one or more additional dosing cycles on or about Day 1 of the one or more additional dosing cycles.

In some instances, the bispecific antibody is administered subcutaneously to the subject. In this embodiment, the bispecific antibody is administered at a dose of between about 0.5 mg to about 40 mg, in some embodiments, the bispecific antibody is administered at a dose of between about 1.0 to about 20 mg, between about 1.0 to about 10 mg, or between about 1.0 to about 5 mg. In one embodiment, the bispecific antibody is administered in a dose of 1.6 mg. Subsequent doses are administered in amounts equal to the initial subcutaneous dose.

In some instances, the bispecific anti-CD20/anti-CD3 antibody is administered to the subject as a monotherapy.

In other instances, the bispecific anti-CD20/anti-CD3 antibody is administered to the subject in a combination therapy. For example, the bispecific anti-CD20/anti-CD3 antibody may be co-administered with one or more additional therapeutic agents. In one instance, the therapeutic agent is another antibody targeting CD20. In one instance, the bispecific anti-CD20/anti-CD3 antibody co-administered with one or more antibodies targeting CD20 selected from the chimeric monoclonal CD20 antibody rituximab (RITUXAN®) or the monoclonal CD20 antibody obinutuzumab (GAZYVA®), in some instances, the bispecific anti-CD20/anti-CD3 antibody is co-administered with rituximab. In some instances, the bispecific anti-CD20/anti-CD3 antibody is co-administered with obinutuzumab. In some instances, the bispecific anti-CD20/anti-CD3 antibody is co-administered with obinutuzumab and rituximab. In other instances, the bispecific anti-CD20/anti-CD3 antibody is co-administered with tocilizumab (ACTEMRA®/RoACTEMRA®).

In some instances, the methods described above include administering the bispecific anti-CD20/anti-CD3 antibody, with or without a CD20 monoclonal antibody, with a further chemotherapy agent and/or an antibody-drug conjugate (ADO). In some instances, the bispecific anti-CD20/anti-CD3 antibody is co-administered with one or more additional chemotherapy agents selected from cyclophosphamide, doxorubicin, vincristine, and prednisolone (CHOP). In some instances, the bispecific anti-CD20/anti-CD3 antibody is co-administered with an ADO. In some instances, the bispecific anti-CD20/anti-CD3 antibody is co-administered with CHOP, wherein vincristine is replaced with an ADC. In some instances, the bispecific anti-CD20/anti-CD3 antibody is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate.

In some instances, the therapeutic agent is a biological modifier. In one instance, the bispecific anti-CD20/anti-CD3 antibody is co-administered with one or more biological modifiers selected from a BCL-2 inhibitor (such as GDC-0199/ABT-199), lenalidomide (REVLIMID®), a PI3K-delta inhibitor (such as idelalisib (ZYDELIG®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or YERVOY®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, for example, the bispecific anti-CD20/anti-CD3 antibody is administered to the subject in a combination therapy that includes a PD-1 axis binding antagonist. The PD-1 axis binding antagonist may be administered prior to, subsequent to, and/or concurrently with the bispecific anti-CD20/anti-CD3 antibody. The PD-1 axis binding antagonist may, in some instances, be a PD-1 binding antagonist, a PD-L1 binding antagonist, or a PD-L2 binding antagonist.

In some instances, the PD-1 binding antagonist is an anti-PD-1 antibody. For example, in some particular instances, the anti-PD-L1 antibody is atezolizumab (CAS Registry Number: 1422185-06-5). Atezolizumab (Genentech) is also known as MPDL3280A.

Atezolizumab comprises: (a) an HVR-H1, HVR-H2, and HVR-H3 sequence of GFTFSDSWIH (SEQ ID NO: 33), AWISPYGGSTYYADSVKG (SEQ ID NO: 34) and RHWPGGFDY (SEQ ID NO: 35), respectively, and (b) an HVR-L1, HVR-L2, and HVR-L3 sequence of RASQDVSTAVA (SEQ ID NO: 36), SASFLYS (SEQ ID NO: 37) and QQYLYHPAT (SEQ ID NO: 38), respectively.

Atezolizumab comprises a heavy chain and a light chain sequence, wherein: (a) the heavy chain variable region sequence comprises the amino acid sequence: EVQLVESGGGLVQPGGSLRLSCAASGFTFSDSWIHWVRQAPGKGLEWVAWISPYGGSTYYADSVKGRF TISADTSKNTAYLQMNSLRAEDTAVYYCARRHWPGGFDYWGQGTLVTVSS (SEQ ID NO: 39), and (b) the light chain variable region sequence comprises the amino acid sequence: DIQMTQSPSSLSASVGDRVTITCRASQDVSTAVAWYQQKPGKAPKLLIYSASFLYSGVPSRFSGSGSGTD FTLTISSLQPEDFATYYCQQYLYHPATFGQGTKVEIKR (SEQ ID NO: 40).

Atezolizumab comprises a heavy chain and a light chain sequence, wherein: (a) the heavy chain comprises the amino acid sequence: EVQLVESGGGLVQPGGSLRLSCAASGFTFSDSWIHWVRQAPGKGLEWVAWISPYGGSTYYADSVKGRF TISADTSKNTAYLQMNSLRAEDTAVYYCARRHWPGGFDYWGQGTLVTVSSASTKGPSVFPLAPSSKSTS GGTAALGCLVKDYFPEPVTVSWNSGALTSGVHTFPAVLQSSGLYSLSSVVTVPSSSLGTQTYCNVNHKP SNTKVDKKVEPKSCDKTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTPPVLDSDGSFFLYSKLTVDKS RWQQGNVFSCSVMHEALHNHYTQKSLSLSPG (SEQ ID NO: 41), and (b) the light chain comprises the amino acid sequence: DIQMTQSPSSLSASVGDRVTITCRASQDVSTAVAWYQQKPGKAPKLLIYSASFLYSGVPSRFSGSGSGTD FTLTISSLQPEDFATYYCQQYLYHPATFGQGTKVEIKRTVAAPSVFIFPPSDEQLKSGTASVVCLLNNFYP REAKVQWKVDNALQSGNSQESVTEQDSKDSTYSLSSTLTLSKADYEKHKVYACEVTHQGLSSPVTKSFN RGEC (SEQ ID NO: 42).

Accordingly, in some instances, the methods include administering the bispecific anti-CD20/anti-CD3 antibody, with or without a CD20 monoclonal antibody, with atezolizumab. In some instances, a dose of atezolizumab is administered concurrently with the C2D1 of the bispecific antibody on Day 1 of the second dosing cycle. In some instances, a first dose of atezolizumab is administered concurrently with the C2D1 of the bispecific antibody on Day 1 of the second dosing cycle (i.e., the subject is not administered atezolizumab in the context of the dosing regimen prior to its concurrent dosing with the C2D1 of the bispecific anti-CD20/anti-CD3 antibody). In some instances, the methods further include administering to the subject atezolizumab concurrently with the single dose of the bispecific anti-CD20/anti-CD3 antibody of the one or more additional dosing cycles on Day 1 of the one or more additional dosing cycles. In some instances, atezolizumab is only administered to the subject concurrently with the bispecific anti-CD20/anti-CD3 antibody. In any of the above instances, each dose of atezolizumab may be about 1200 mg.

Accordingly, in some instances, the invention provides a method of treating a subject having a cancer (e.g., a B cell proliferative disorder) comprising administering to the subject a bispecific antibody that binds to CD20 and CD3 in a dosing regimen comprising at least a first dosing cycle and a second dosing cycle, (a) the first dosing cycle comprising a first dose (C1D1), a second dose (C1D2), and a third dose (C1D3) of the bispecific antibody, wherein the C1D1 and the C1D2 are each no greater than the C1D3, and the C1D1 is between about 0.02 mg to about 4.0 mg (e.g., about 0.8 or 1.0 mg), the C1D2 is between about 0.05 mg to about 20.0 mg (e.g., about 1 mg or 2 mg), and the C1D3 is between about 0.2 mg to about 50.0 mg (e.g., between about 2 mg to about 10 mg, e.g., about 3.0 mg, 4.2 mg, or 6.0 mg), and (b) the second dosing cycle comprises a single dose (C2D1) of the bispecific antibody, wherein the C2D1 is approximately equal to or greater than the C1D3 and is between about 0.2 mg to about 50.0 mg (e.g., between about 2 mg to about 10 mg, e.g., about 3.0 mg, 4.2 mg, or 6.0 mg), and wherein the length of each dosing cycle of the dosing regimen is 21 days; the C1D1, the C1D2, and the C1D3 is administered on or about Days 1, 8, and 15, respectively, of the first dosing cycle; the C2D1 of the bispecific antibody is administered concurrently with a first dose of about 1200 mg of atezolizumab on Day 1 of the second dosing cycle; and the dosing regimen optionally includes one to six additional dosing cycles, each 21 days in length, and each including a single dose of the bispecific antibody that is approximately equal to the C2D1, which is concurrently administered with a single dose of about 1200 mg of atezolizumab, on Day 1 of each of the one to six additional dosing cycles. Atezolizumab may only be administered to the subject concurrently with the bispecific anti-CD20/anti-CD3 antibody in the dosing regimen. In such instances, the method may include administration of one or more additional therapeutic agents in the context of the dosing regimen. For example, in a particular instance, the bispecific anti-CD20/anti-CD3 antibody can be co-administered with obinutuzumab (GAZYVA®) or tocilizumab (ACTEMRA®/RoACTEMRA®), wherein the patient is first administered with obinutuzumab (GAZYVA®) or tocilizumab (ACTEMRA®/RoACTEMRA®) and then separately administered with the bispecific anti-CD20/anti-CD3 antibody (e.g., the patient is pre-treated with obinutuzumab (GAZYVA®) or tocilizumab (ACTEMRA®/RoACTEMRA®)).

In some instances, the PD-1 binding antagonist is another anti-PD-1 antibody, such as an anti-PD-1 antibody selected from the group consisting of MDX-1106 (nivolumab), MK-3475 (pembrolizumab), CT-011 (pidilizumab), MEDI-0680 (AMP-514), PDR001, REGN2810, and BGB-108. MDX-1106, also known as MDX-1106-04, ONO-4538, BMS-936558, or nivolumab, is an anti-PD-1 antibody described in PCT Pub. No. WO 2006/121168. MK-3475, also known as pembrolizumab or lambrolizumab, is an anti-PD-1 antibody described in PCT Pub. No. WO 2009/114335. CT-011, also known as hBAT, hBAT-1 or pidilizumab, is an anti-PD-1 antibody described in PCT Pub. No. WO 2009/101611. In other instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In other instances, the PD-1 binding antagonist is AMP-224. AMP-224, also known as B7-DCIg, is a PD-L2-Fc fusion soluble receptor described in PCT Pub. Nos. WO 2010/027827 and WO 2011/066342.

In other instances, the anti-PD-L1 antibody is selected from YW243.55.S70, MDX-1105, and MEDI4736 (durvalumab), and MSB0010718C (avelumab). Antibody YW243.55.S70 is an anti-PD-L1 described in PCT Pub. No. WO 2010/077634. MDX-1105, also known as BMS-936559, is an anti-PD-L1 antibody described in PCT Pub. No. WO 2007/005874. MEDI4736 (durvalumab) is an anti-PD-L1 monoclonal antibody described in PCT Pub. No. WO 2011/066389 and U.S. Pub. No. 2013/034559. Examples of anti-PD-L1 antibodies useful for the methods of this invention, and methods for making thereof are described in PCT Pub. Nos. WO 2010/077634, WO 2007/005874, and WO 2011/066389, and also in U.S. Pat. No. 8,217,149, and U.S. Pub. No. 2013/034559, which are incorporated herein by reference.

In other instances, the PD-L2 binding antagonist is an anti-PD-L2 antibody (e.g., a human, a humanized, or a chimeric anti-PD-L2 antibody). In some instances, the PD-L2 binding antagonist is an immunoadhesin.

In some instances, the bispecific anti-CD20/anti-CD3 antibody is co-administered with rituximab and one or more chemotherapy agents. In one instance, the bispecific anti-CD20/anti-CD3 antibody is co-administered with rituximab and CHOP. In one instance, the bispecific anti-CD20/anti-CD3 antibody is co-administered with rituximab and an ADC. In one instance, the bispecific anti-CD20/anti-CD3 antibody is co-administered with rituximab and CHOP, wherein vincristine is replaced with an ADC. In one instance, the bispecific anti-CD20/anti-CD3 antibody is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate.

In some instances, the bispecific anti-CD20/anti-CD3 antibody is co-administered with rituximab and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or YERVOY®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody is co-administered with rituximab, one or more chemotherapy agents, and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as I-D-MT)), TIGIT, MICA/B, GITR (e.g., TRX518) or arginase, ipilimumab (also known as MDX-010, MDX-101, or YERVOY®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody is co-administered with rituximab, an ADC, and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or YERVOY®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody is co-administered with obinutuzumab and one or more chemotherapy agents. In one instance, the bispecific anti-CD20/anti-CD3 antibody is co-administered with obinutuzumab and CHOP. In one instance, the bispecific anti-CD20/anti-CD3 antibody is co-administered with obinutuzumab and an ADC. In one instance, the bispecific anti-CD20/anti-CD3 antibody is co-administered with obinutuzumab and CHOP, wherein vincristine is replaced with an ADC. In one instance, the bispecific anti-CD20/anti-CD3 antibody is co-administered with an ADC selected from an anti-CD79b antibody drug conjugate (such as anti-CD79b-MC-vc-PAB-MMAE or the anti-CD79b antibody drug conjugate described in any one of U.S. Pat. No. 8,088,378 and/or US 2014/0030280, or polatuzumab vedotin), an anti-CD19 antibody drug conjugate, an anti-CD22 antibody drug conjugate, an anti-CD45 antibody drug conjugate, and an anti-CD32 drug conjugate. In one instance, the bispecific anti-CD20/anti-CD3 antibody is co-administered with obinutuzumab and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or YERVOY®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the bispecific anti-CD20/anti-CD3 antibody is co-administered with obinutuzumab, an ADC, and one or more biological modifiers selected from a BCL-2 inhibitor (such as GDC-0199/ABT-199), lenalidomide (REVLIMID®), a PI3K-delta inhibitor (such as idelalisib (ZYDELIG®)), a PD-1 axis binding antagonist, an agonist, e.g., agonist antibody, directed against an activating co-stimulatory molecule, e.g., CD40, CD226, CD28, OX40 (e.g., AgonOX), GITR, CD137 (also known as TNFRSF9, 4-1BB, or ILA), CD27 (e.g., CDX-1127), HVEM, or CD127, an antagonist, e.g., antagonist antibody, directed against an inhibitory co-stimulatory molecule, e.g., CTLA-4 (also known as CD152), PD-1, TIM-3, BTLA, VISTA, LAG-3, B7-H3, B7-H4, IDO (e.g., 1-methyl-D-tryptophan (also known as 1-D-MT)), TIGIT, MICA/B, GITR (e.g., TRX518) or arginase, ipilimumab (also known as MDX-010, MDX-101, or YERVOY®), tremelimumab (also known as ticilimumab or CP-675,206, urelumab (also known as BMS-663513), MGA271, an antagonist directed against a TGF beta, e.g., metelimumab (also known as CAT-192), fresolimumab (also known as GC1008), LY2157299k, and an adoptive transfer of a T cell (e.g., a cytotoxic T cell or CTL) expressing a chimeric antigen receptor (CAR), e.g., adoptive transfer of a T cell comprising a dominant-negative TGF beta receptor, e.g., a dominant-negative TGF beta type II receptor.

In some instances, the additional therapy includes an alkylating agent. In one instance, the alkylating agent is 4-[5-[bis(2-chloroethyl)amino]-methylbenzimidazol-2-yl]butanoic acid and salts thereof. In one instance, the alkylating agent is bendamustine.

In some instances, the additional therapy comprises a BCL-2 inhibitor. In one embodiment, the BCL-2 inhibitor is 4-(4-{[2-(4-chlorophenyl)-4,4-dimethylcyclohex-1-en-1-yl]methyl}piperazin-1-yl)-N-({3-nitro-4-[(tetrahydro-2H- pyran-4-ylmethyl)amino]phenyl}sulfonyl)-2-(1H-pyrrolo [2,3-b]pyridin-5-yloxy)benzamide and salts thereof. In one instance, the BCL-2 inhibitor is venetoclax (CAS #: 1257044-40-8).

In some instances, the additional therapy comprises a phosphoinositide 3-kinase (PI3K) inhibitor. In one instance, the PI3K inhibitor inhibits delta isoform PI3K (i.e., P1105). In some instances, the PI3K inhibitor is 5-Fluoro-3-phenyl-2-[(1S)-1-(7H-purin-6-ylamino)propyl]-4(3H)-quinazolinone and salts thereof. In some instances, the PI3K inhibitor is idelalisib (CAS #: 870281-82-6). In one instance, the PI3K inhibitor inhibits alpha and delta isoforms of PI3K. In some instances, the PI3K inhibitor is 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide and salts thereof.

In a further aspect of the invention, the additional therapy comprises a Bruton's tyrosine kinase (BTK) inhibitor. In one instance, the BTK inhibitor is 1-[(3R)-3-[4-Amino-3-(4-phenoxyphenyl)-1H-pyrazolo[3,4-d]pyrimidin-1-yl]piperidin-1-yl]prop-2-en-1-one and salts thereof. In one instance, the BTK inhibitor is ibrutinib (CAS #: 936563-96-1).

In some instances, the additional therapy comprises thalidomide or a derivative thereof. In one instance, the thalidomide or a derivative thereof is (RS)-3-(4-Amino-1-oxo-1,3-dihydro-2H-isoindol-2-yl)piperidine-2,6-dione and salts thereof. In one instance, the thalidomide or a derivative thereof is lendalidomide (CAS #: 191732-72-6).

In instances for which the methods described herein involve a combination therapy, such as a particular combination therapy noted above, the combination therapy encompasses the co-administration the bispecific anti-CD20/anti-CD3 antibody with one or more additional therapeutic agents, and such co-administration may be combined administration (where two or more therapeutic agents are included in the same or separate formulations) or separate administration, in which case, administration of the anti-CD20/anti-CD3 bispecific antibody can occur prior to, simultaneously, and/or following, administration of the additional therapeutic agent or agents. In one embodiment, administration of the anti-CD20/anti-CD3 bispecific antibody and administration of an additional therapeutic agent or exposure to radiotherapy can occur within about one month, or within about one, two or three weeks, or within about one, two, three, four, five, or six days, of each other. In a particular instance, the bispecific anti-CD20/anti-CD3 antibody can be co-administered with obinutuzumab (GAZYVA®), wherein the patient is first administered with obinutuzumab (GAZYVA®) and then separately administered with the bispecific anti-CD20/anti-CD3 antibody (e.g., the patient is pre-treated with obinutuzumab (GAZYVA®)). In another particular instance, the bispecific anti-CD20/anti-CD3 antibody can be co-administered with tocilizumab (ACTEMRA®/RoACTEMRA®), wherein the patient is first administered with tocilizumab (ACTEMRA®/RoACTEMRA)) and then separately administered with the bispecific anti-CD20/anti-CD3 antibody (e.g., the patient is pre-treated with tocilizumab (ACTEMRA®/RoACTEMRA®)).

Any of the methods of the invention described herein may be useful for treating cancer, such as hematologic cancer, including B cell proliferative disorders/malignancies. In particular, B cell proliferative disorders amenable to treatment with a bispecific anti-CD20/anti-CD3 antibody in accordance with the methods described herein include, without limitation, non-Hodgkin's lymphoma (NHL), including diffuse large B cell lymphoma (DLBCL), which may be relapsed or refractory DLBCL, as well as other cancers including germinal-center B cell-like (GCB) diffuse large B cell lymphoma (DLBCL), activated B cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic lymphoma (SLL), lymphoplasmacytic lymphoma (LL), Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, Waldenström macroglobulinemia, heavy chain diseases, a heavy chain disease, γ heavy chain disease, p heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, primary mediastinal (thymic) large B cell lymphoma (PMLBCL), intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and Burkitt lymphoma, and B cell lymphoma, unclassifiable, with features intermediate between DLBCL and classical Hodgkin's lymphoma. Further examples of B cell proliferative disorders include, but are not limited to, multiple myeloma (MM); low grade/follicular NHL; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NI-HL; AIDS-related lymphoma; and acute lymphoblastic leukemia (ALL); chronic myeloblastic leukemia; and post-transplant lymphoproliferative disorder (PTLD). In particular instances, the B cell proliferative disorder may be NHL (e.g., DLBCL (e.g., relapsed or refractory DLBCL), PMLBCL, or FL) or CLL.

The methods described herein may result in an improved benefit-risk profile for patients having cancer (e.g., a B cell proliferative disorder, e.g., NHL, (e.g., DLBCL (e.g., relapsed or refractory DLBCL), PMLBCL, or FL) or CLL) being treated with an anti-CD20/anti-CD3 bispecific antibody. In some instances, treatment using the methods described herein that result in administering the anti-CD20/anti-CD3 bispecific antibody in the context of a fractionated, dose-escalation dosing regimen results in a reduction (e.g., by 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater) or complete inhibition (100% reduction) of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the fractionated, dose-escalation dosing regimen of the invention relative to treatment with an anti-CD20/anti-CD3 bispecific antibody using an non-fractioned dosing regimen.

The methods may involve administering the anti-CD20/anti-CD3 bispecific antibody (and/or any additional therapeutic agent) by any suitable means, including parenteral, intrapulmonary, and intranasal, and, if desired for local treatment, intralesional administration. Parenteral infusions include intravenous, subcutaneous, intramuscular, intraarterial, and intraperitoneal administration routes. In some embodiments, the anti-CD20/anti-CD3 bispecific antibody is administered by intravenous infusion. In other instances, the anti-CD20/anti-CD3 bispecific antibody is administered subcutaneously. In some instances, the anti-CD20/anti-CD3 bispecific antibody administered by intravenous injection exhibits a less toxic response (i.e., fewer unwanted effects) in a patient than the same anti-CD20/anti-CD3 bispecific antibody administered by subcutaneous injection, or vice versa.

For all the methods described herein, the anti-CD20/anti-CD3 bispecific antibody would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The anti-CD20/anti-CD3 bispecific antibody need not be, but is optionally formulated with, one or more agents currently used to prevent or treat the disorder in question. The effective amount of such other agents depends on the amount of the anti-CD20/anti-CD3 bispecific antibody present in the formulation, the type of disorder or treatment, and other factors discussed above. The anti-CD20/anti-CD3 bispecific antibody may be suitably administered to the patient over a series of treatments.

In the event that the subject has an adverse cytokine release syndrome (CRS) event following commencement of any of the methods described above, the methods may involve additional measures to treat the CRS event.

The National Cancer Institute (NCI) Common Terminology Criteria for Adverse Events (CTCAE) v4.0 includes a grading system for CRS, which was subsequently revised by Lee et al. (*Blood.* 124(2): 188-95, 2014) to define mild, moderate, severe, or life-threatening CRS regardless of the inciting agent. This revised CRS grading system is shown in Table 1 below.

TABLE 1

CRS Grading System

| Grade | Toxicity |
| --- | --- |
| Grade 1 | Symptoms are not life-threatening and require symptomatic treatment only, e.g., fever, nausea, fatigue, headache, myalgias, malaise |
| Grade 2 | Symptoms require and respond to moderate intervention<br>Oxygen requirement <40% or<br>Hypotension responsive to fluids or low dose of one vasopressor or Grade 2 organ toxicity |
| Grade 3 | Symptoms require and respond to aggressive intervention<br>Oxygen requirement ≥40% or<br>Hypotension requiring high dose or multiple vasopressors or Grade 3 organ toxicity or grade 4 transaminitis |

TABLE 1-continued

CRS Grading System

| Grade | Toxicity |
| --- | --- |
| Grade 4 | Life-threatening symptoms<br>Requirement for ventilator support or<br>Grade 4 organ toxicity (excluding transaminitis) |
| Grade 5 | Death |

As indicated in Table 1, CRS can result in significant disability or death if unsuccessfully managed. Current clinical management focuses on treating the individual signs and symptoms, providing supportive care, and attempting to dampen the inflammatory response using a high dose of corticosteroids. However, this approach is not always successful, especially in the case of late intervention. CRS observed in patients during the double-step fractionated, dose-escalation dosing regimen may be alternatively managed.

CRS is associated with elevations in a wide array of cytokines, including marked elevations in IFNγ, IL-6, and TNF-α levels. Emerging evidence implicates IL-6, in particular, as a central mediator in CRS. IL-6 is a proinflammatory, multi-functional cytokine produced by a variety of cell types, which has been shown to be involved in a diverse array of physiological processes, including T cell activation. Regardless of the inciting agent, CRS is associated with high IL-6 levels (Nagorsen et al. *Cytokine.* 25(1): 31-5, 2004; Lee et al. *Blood* 124(2): 188-95, 2014); Doesegger et al. *Clin. Transl. Immunology.* 4(7): e39, 2015), and IL-6 correlates with the severity of CRS, with patients who experience a grade 4 or 5 CRS event having much higher IL-6 levels compared to patients who do not experience CRS or experience milder CRS (grades 0-3) (Chen et al. *J. Immunol. Methods.* 434:1-8, 2016). Therefore, blocking the inflammatory action of IL-6 using an agent that inhibits IL-6-mediated signaling to manage CRS observed in patients during the double-step fractionated, dose-escalation dosing regimen is an alternative to steroid treatment that would not be expected to negatively impact T cell function or diminish the efficacy or clinical benefit of anti-CD20/anti-CD3 bispecific antibody therapy in the treatment of B cell proliferative disorders.

Tocilizumab (ACTEMRA®/RoACTEMRA®) is a recombinant, humanized, anti-human monoclonal antibody directed against soluble and membrane-bound IL-6R, which inhibits IL-6-mediated signaling (see, e.g., WO 1992/019579, which is incorporated herein by reference in its entirety).

If the subject has a cytokine release syndrome (CRS) event following administration of the bispecific antibody, the method may further involve administering to the subject an effective amount of an interleukin-6 receptor (IL-6R) antagonist (e.g., an anti-IL-6R antibody, e.g., tocilizumab (ACTEMRA®/RoACTEMRA®)) to manage the event. In some instances, tocilizumab is administered intravenously to the subject as a single dose of about 8 mg/kg. Other anti-IL-6R antibodies that could be used instead of, or in combination with, tocilizumab include sarilumab, vobarilizumab (ALX-0061), SA-237, and variants thereof.

If the subject has a CRS event that does not resolve or worsens within 24 hours of administering the IL-6R antagonist to treat the symptoms of the CRS event, and the method may further comprise administering to the subject one or more additional doses of the IL-6R antagonist (e.g., an anti-IL-6R antibody, e.g., tocilizumab) to manage the CRS event. The subject may be administered a corticosteroid, such as methylprednisolone or dexamethasone if CRS event is not managed through administration of the IL-6R antagonist.

Management of the CRS events may be tailored based on the Stage of the CRS and the presence of comorbidities. For example, if the subject has a grade 2 cytokine release syndrome (CRS) event in the absence of comorbidities or in the presence of minimal comorbidities following administration of the bispecific antibody, the method may further include treating the symptoms of the grade 2 CRS event while suspending treatment with the bispecific antibody. If the grade 2 CRS event then resolves to a grade ≤1 CRS event for at least three consecutive days, the method may further include resuming treatment with the bispecific antibody without altering the dose. On the other hand, if the grade 2 CRS event does not resolve or worsens to a grade ≥3 CRS event within 24 hours of treating the symptoms of the grade 2 CRS event, the method may further involve administering to the subject an effective amount of an interleukin-6 receptor (IL-6R) antagonist (e.g., an anti-IL-6R antibody, e.g., tocilizumab (ACTEMRA®/RoACTEMRA®)) to manage the grade 2 or grade ≥3 CRS event. In some instances, tocilizumab is administered intravenously to the subject as a single dose of about 8 mg/kg. Other anti-IL-6R antibodies that could be used instead of, or in combination with, tocilizumab include sarilumab, vobarilizumab (ALX-0061), SA-237, and variants thereof.

If the subject has a grade 2 CRS event in the presence of extensive comorbidities following administration of the bispecific antibody, the method may further include administering to the subject a first dose of an IL-6R antagonist (e.g., an anti-IL-6R antibody, e.g., tocilizumab (ACTEMRA®/RoACTEMRA®)) to manage the grade 2 CRS event while suspending treatment with the bispecific antibody. In some instances, the first dose of tocilizumab is administered intravenously to the subject at a dose of about 8 mg/kg. Other anti-IL-6R antibodies that could be used instead of, or in combination with, tocilizumab include sarilumab, vobarilizumab (ALX-0061), SA-237, and variants thereof. In some instances, if the grade 2 CRS event resolves to a grade ≤1 CRS event within two weeks, the method further includes resuming treatment with the bispecific antibody at a reduced dose. In some instances, the reduced dose is the next highest cleared dose of the bispecific antibody in the first dosing cycle of a non-fractionated, dose-escalation dosing regimen. If, on the other hand, the grade 2 CRS event does not resolve or worsens to a grade ≥3 CRS event within 24 hours of treating the symptoms of the grade 2 CRS event, the method may further include administering to the subject one or more (e.g., one, two, three, four, or five or more) additional doses of an IL-SR antagonist (e.g., an anti-IL-6R antibody, e.g., tocilizumab) to manage the grade 2 or grade ≥3 CRS event. In some particular instances, the grade 2 CRS event does not resolve or worsens to a grade ≥3 CRS event within 24 hours of treating the symptoms of the grade 2 CRS event, and the method may further include administering to the subject one or more additional doses of tocilizumab to manage the grade 2 or grade ≥3 CRS event. In some instances, the one or more additional doses of tocilizumab is administered intravenously to the subject at a dose of about 1 mg/kg to about 15 mg/kg, e.g., about 4 mg/kg to about 10 mg/kg, e.g., about 6 mg/kg to about 10 mg/kg, e.g., about 8 mg/kg. In some instances, the method further includes administering to the subject an effective amount of a corticosteroid. The corticosteroid may be administered before, after, or concurrently with the one or more additional doses of tocilizumab or other anti-IL-6R antibody. In some instances, the corticosteroid is administered intravenously to the subject. In some instances, the corticosteroid is methylprednisolone. In some instances, the methylprednisolone is administered at a dose of about 1 mg/kg per day to about 5 mg/kg per day, e.g., about 2 mg/kg per day. In some instances, the corticosteroid is dexamethasone. In some instances, the dexamethasone is administered at a dose of about 10 mg (e.g., a single dose of about 10 mg intravenously).

If the subject has a grade 3 CRS event following administration of the bispecific antibody, the method may further include administering to the subject a first dose of an IL-6R antagonist (e.g., an anti-IL-6R antibody, e.g., tocilizumab (ACTEMRA®/RoACTEMRA®)) to manage the grade 3 CRS event while suspending treatment with the bispecific antibody. In some instances, the first dose of tocilizumab is administered intravenously to the subject at a dose of about 8 mg/kg. Other anti-IL-6R antibodies that could be used instead of, or in combination with, tocilizumab include sarilumab, vobarilizumab (ALX-0061), SA-237, and variants thereof. In some instances, the grade 3 CRS event resolves to a grade ≤1 CRS event within two weeks, and the method further includes resuming treatment with the bispecific antibody at a reduced dose. In some instances, the reduced dose is the next highest cleared dose of the bispecific antibody in the first dosing cycle of a non-fractionated, dose-escalation dosing regimen. In other instances, if the grade 3 CRS event does not resolve or worsens to a grade 4 CRS event within 24 hours of treating the symptoms of the grade 3 CRS event, the method may further include administering to the subject one or more (e.g., one, two, three, four, or five or more) additional doses of an IL-6R antagonist (e.g., an anti-IL-6R antibody, e.g., tocilizumab) to manage the grade 3 or grade 4 CRS event. In some particular instances, the grade 3 CRS event does not resolve or worsens to a grade 4 CRS event within 24 hours of treating the symptoms of the grade 3 CRS event, and the method further includes administering to the subject one or more additional doses of tocilizumab to manage the grade 3 or grade 4 CRS event. In some instances, the one or more additional doses of tocilizumab is administered intravenously to the subject at a dose of about 1 mg/kg to about 15 mg/kg, e.g., about 4 mg/kg to about 10 mg/kg, e.g., about 6 mg/kg to about 10 mg/kg, e.g., about 8 mg/kg. In some instances, the method further includes administering to the subject an effective amount of a corticosteroid. The corticosteroid may be administered before, after, or concurrently with the one or more additional doses of tocilizumab or other anti-IL-6R antibody. In some instances, the corticosteroid is administered intravenously to the subject. In some instances, the corticosteroid is methylprednisolone. In some instances, the methylprednisolone is administered at a dose of about 1 mg/kg per day to about 5 mg/kg per day, e.g., about 2 mg/kg per day. In some instances, the corticosteroid is dexamethasone. In some instances, the dexamethasone is administered at a dose of about 10 mg (e.g., a single dose of about 10 mg intravenously).

If the subject has a grade 4 CRS event following administration of the bispecific antibody, the method may further include administering to the subject a first dose of an IL-6R antagonist (e.g., an anti-IL-6R antibody, e.g., tocilizumab (ACTEMRA®/RoACTEMRA®)) to manage the grade 4 CRS event and permanently discontinuing treatment with the bispecific antibody. In some instances, the first dose of tocilizumab is administered intravenously to the subject at a dose of about 8 mg/kg. Other anti-IL-6R antibodies that could be used instead of, or in combination with, tocilizumab include sarilumab, vobarilizumab (ALX-0061), SA-237, and variants thereof. The grade 4 CRS event, in some instances, may resolve within 24 of treating the symptoms of the grade 4 CRS event. In other instances, if the grade 4 CRS event does not resolve within 24 hours of treating the symptoms of the grade 4 CRS event, the method may further include administering to the subject one or more additional doses of an IL-6R antagonist (e.g., an anti-IL-6R antibody, e.g., tocilizumab (ACTEMRA®/RoACTEMRA®) to manage the grade 4 CRS event. In some particular instances, the grade 4 CRS event does not resolve within 24 hours of treating the symptoms of the grade 4 CRS event, and the method further includes administering to the subject one or more (e.g., one, two, three, four, or five or more) additional doses of tocilizumab to manage the grade 4 CRS event. In some instances, the one or more additional doses of tocilizumab is administered intravenously to the subject at a dose of about 1 mg/kg to about 15 mg/kg, e.g., about 4 mg/kg to about 10 mg/kg, e.g., about 6 mg/kg to about 10 mg/kg, e.g., about 8 mg/kg. In some instances, the method further includes administering to the subject an effective amount of a corticosteroid. The corticosteroid may be administered before, after, or concurrently with the one or more additional doses of tocilizumab or other anti-IL-6R antibody. In some instances, the corticosteroid is administered intravenously to the subject. In some instances, the corticosteroid is methylprednisolone. In some instances, the methylprednisolone is administered at a dose of about 1 mg/kg per day to about 5 mg/kg per day, e.g., about 2 mg/kg per day. In some instances, the corticosteroid is dexamethasone. In some instances, the dexamethasone is administered at a dose of about 10 mg (e.g., a single dose of about 10 mg intravenously).

A. Anti-CD20/Anti-CD3 Bispecific Antibodies

The methods described herein include administering to a subject having cancer (e.g., a B cell proliferative disorder, e.g., non-Hodgkin's lymphoma (NHL), e.g., diffuse large B-cell lymphoma (DLBCL), e.g., relapsed or refractory DLBCL) a bispecific antibody that binds to CD20 and CD3 (i.e., an anti-CD20/anti-CD3 antibody).

In some instances, any of the methods described herein may include administering a bispecific antibody that includes an anti-CD20 arm having a first binding domain comprising at least one, two, three, four, five, or six hypervariable regions (HVRs) selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of WYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively. In some instances, the bispecific antibody comprises an anti-CD20 arm comprising a first binding domain comprising (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b). Accordingly, in some instances, the first binding domain comprises a VH domain comprising an amino acid sequence of SEQ ID NO: 7 and a VL domain comprising an amino acid sequence of SEQ ID NO: 8.

In some instances, any of the methods described herein may include administering a bispecific antibody that includes an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYSNYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, the anti-CD20/anti-CD3 bispecific antibody comprises at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, the bispecific antibody comprises an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). Accordingly, in some instances, the second binding domain comprises a VH domain comprising an amino acid sequence of SEQ ID NO: 15 and a VL domain comprising an amino acid sequence of SEQ ID NO: 16.

In some instances, any of the methods described herein may include administering a bispecific antibody that includes (1) an anti-CD20 arm having a first binding domain comprising at least one, two, three, four, five, or six HVRs selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of WYYSNSYWYFDV (SEQ ID NO:3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6); and (2) an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYSNYYFDY (SEQ ID NO:

11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, the anti-CD20/anti-CD3 bispecific antibody comprises (1) at least one (e.g., 1, 2, 3, or 4) of heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively, and (2) at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L2, FR-L3, and FR-L4 comprising the sequences of SEQ ID NOs: 29-32, respectively. In some instances, the anti-CD20/anti-CD3 bispecific antibody comprises (1) an anti-CD20 arm comprising a first binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b), and (2) an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). In some instances, the anti-CD20/anti-CD3 bispecific antibody comprises (1) a first binding domain comprising a VH domain comprising an amino acid sequence of SEQ ID NO: 7 and a VL domain comprising an amino acid sequence of SEQ ID NO: 8 and (2) a second binding domain comprising a VH domain comprising an amino acid sequence of SEQ ID NO: 15 and a VL domain comprising an amino acid sequence of SEQ ID NO: 16.

The anti-CD20/anti-CD3 bispecific antibody may be produced using recombinant methods and compositions, for example, as described in U.S. Pat. No. 4,816,567.

In some instances, the anti-CD20/anti-CD3 bispecific antibody according to any of the above embodiments described above may incorporate any of the features, singly or in combination, as described in Sections 1-5 below.

1. Antibody Affinity

In certain embodiments, the bispecific antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-8}$ M to $10^{-13}$ M) with respect to CD20, CD3, or both.

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{on}/k_{off}$. See, for example, Chen et al., *J. Mol. Biol* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, the anti-CD20/anti-CD3 bispecific antibody is an antibody fragment, e.g., an antibody fragment that binds to CD20 and CD3. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134 (2003); and Hollinger et al. *Proc. Natl. Acad. Sci. USA* 90: 6444-6448 (1993). Triabodies and tetrabodies are also described in Hudson et al. *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an anti-CD20/anti-CD3 antibody for use in accordance with the methods described herein is a chimeric antibody. Certain chimeric antibodies are described, e.g., in U.S. Pat. No. 4,816,567; and Morrison et al. *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et. al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Nat. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Knob-in-Hole Bispecific Antibody Engineering

The anti-CD20/anti-CD3 bispecific antibody may be prepared as a full-length antibody or an antibody fragment. Techniques for making bispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). "Knob-in-hole" engineering of bispecific antibodies may be utilized to generate a first arm containing a knob and a second arm containing the hole into which the knob of the first arm may bind. The knob of the bispecific antibodies may be on the anti-CD3 arm in one embodiment. Alternatively, the knob of the bispecific antibodies of the invention may on the anti-CD20 arm. The hole of the bispecific antibodies of the invention may be on the anti-CD3 arm in one embodiment. Alternatively, the hole of the bispecific antibodies of the invention may be on the anti-CD20 arm. In some instances, the anti-CD20/anti-CD3 bispecific antibody produced using knob-in-hole technology may comprise one or more heavy chain constant domains, wherein the one or more heavy chain constant domains are selected from a first CH1 (CH1$_1$) domain, a first CH2 (CH2$_1$) domain, a first CH3 (CH3$_1$) domain, a second CH1 (CH1$_2$) domain, second CH2 (CH2$_2$) domain, and a second CH3 (CH3$_2$) domain. In some instances, at least one of the one or more heavy chain constant domains is paired with another heavy chain constant domain. In some instances, the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain. In some instances, the CH3$_1$ and CH3$_2$ domains meet at an interface between the protuberance and cavity. In some instances, the CH2$_1$ and CH2$_2$ domains each comprise a protuberance or cavity, and wherein the protuberance or cavity in the CH2$_1$ domain is positionable in the cavity or protuberance, respectively, in the CH2$_2$ domain. In some instances, the CH2$_1$ and CH2$_2$ domains meet at an interface between said protuberance and cavity.

Bispecific antibodies may also be engineered using immunoglobulin crossover (also known as Fab domain exchange or CrossMab format) technology (see e.g., WO2009/080253; Schaefer et al., *Proc. Natl. Acad. Sci. USA,* 108: 11187-11192 (2011)). Bispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)): using leucine zippers to produce bispecific antibodies (see, e.g., Kostelny et al., *J. Immunol.*, 148(5):1547-1553 (1992)); using "diabody" technology for making bispecific antibody fragments (see, e.g., Hollinger et al., *Proc. Nat. Acad. Sci. USA*, 90:6444-6448 (1993)); and using single-chain Fv (sFv) dimers (see e.g. Gruber et al., *J. Immunol.*, 152:5368 (1994)); and preparing trispecific antibodies as described, e.g., in Tutt et al. *J. Immunol.*, 147: 60 (1991).

The anti-CD20/anti-CD3 bispecific antibodies, or antibody fragments thereof, may also include a "Dual Acting FAb" or "DAF" comprising an antigen binding site that binds to CD3 as well as CD20 (see, e.g., U.S. Pub. No. 2008/0069820).

5. Anti-CD20/Anti-CD3 Bispecific Antibody Variants

In some instances, amino acid sequence variants of the anti-CD20/anti-CD3 bispecific antibodies described above are envisioned. For example, it may be desirable to improve the binding affinity and/or other biological properties of the bispecific antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 2

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b. Glycosylation Variants

In some instances, the methods of the invention involve administering to the subject in the context of a fractionated, dose-escalation dosing regimen an anti-CD20/anti-CD3 bispecific antibody variant that has been modified to increase or decrease the extent to which the bispecific antibody is glycosylated. Addition or deletion of glycosylation sites to anti-CD20/anti-CD3 antibody of the invention may be conveniently accomplished by altering the amino acid sequence such that one or more glycosylation sites is created or removed.

Where the bispecific antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some instances, the methods involve administering an anti-CD20/anti-CD3 bispecific antibody variant having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704: US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol Bioeng.*, 94(4):680-688 (2006); and WO2003/085107).

In view of the above, in some instances, the methods of the invention involve administering to the subject in the context of a fractionated, dose-escalation dosing regimen an anti-CD20/anti-CD3 bispecific antibody variant that comprises an aglycosylation site mutation. In some instances, the aglycosylation site mutation reduces effector function of the bispecific antibody. In some instances, the aglycosylation site mutation is a substitution mutation. In some instances, the bispecific antibody comprises a substitution mutation in the Fc region that reduces effector function. In some instances, the substitution mutation is at amino acid residue N297, L234, L235, and/or D265 (EU numbering). In some instances, the substitution mutation is selected from the group consisting of N297G, N297A, L234A, L235A, D265A, and P329G. In some instances, the substitution mutation is at amino acid residue N297. In a preferred embodiment, the substitution mutation is N297A.

In other instances, bispecific antibody variants with bisected oligosaccharides are used in accordance with the methods of the invention, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In some instances, an anti-CD20/anti-CD3 bispecific antibody variant that has one or more amino acid modifications introduced into the Fc region (i.e., an Fc region variant (see e.g., US 2012/0251531)) of the bispecific antibody may be administered to a subject having cancer (e.g., a B cell proliferation disorder) in accordance with the methods of the invention. The Fc region variant may comprise a human Fc region sequence (e.g., a human IgG1, IgG2, IgG3 or IgG4 Fc region) comprising an amino acid modification (e.g., a substitution) at one or more amino acid positions.

In some instances, the bispecific Fc region antibody variant possesses some but not all effector functions, which makes it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al. *J. Immunol. Methods* 202: 163 (1996): Cragg, M. S. et al. *Blood.* 101:1045-1052 (2003); and Cragg, M. S. and M. J. Glennie *Blood.* 103: 2738-2743 (2004)). FcRn binding and in vivo clearance/half life determinations can also be performed using methods known in the art (see, e.g., Petkova, S. B. et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain instances, the proline at position 329 of a wild-type human Fc region in the antibody is substituted with glycine or arginine or an amino acid residue large enough to destroy the proline sandwich within the Fc/Fcγ receptor interface that is formed between the proline 329 of the Fc and tryptophan residues Trp 87 and Trp 110 of FcgRIII (Sondermann et al. *Nature.* 406, 267-273 (2000)). In certain embodiments, the bispecific antibody comprises at least one further amino acid substitution. In one embodiment, the further amino acid substitution is S228P, E233P, L234A, L235A, L235E, N297A, N297D, or P331S, and still in another embodiment the at least one further amino acid substitution is L234A and L235A of the human IgG1 Fc region or S228P and L235E of the human IgG4 Fc region (see e.g., US 2012/0251531), and still in another embodiment the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Bio. Chem.* 9(2): 6591-6604 (2001).)

In certain instances, the anti-CD20/anti-CD3 bispecific antibody comprises an Fc region with one or more amino acid substitutions which improve ADCC, e.g., substitutions at positions 298, 333, and/or 334 of the Fc region (EU numbering of residues).

In some instances, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.,* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US20050014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d. Cysteine Engineered Antibody Variants

In certain embodiments, it may be desirable to create cysteine engineered anti-CD20/anti-CD3 bispecific antibodies, e.g., "thioMAbs," in which one or more residues of the bispecific antibody are substituted with cysteine residues. In particular embodiments, the substituted residues occur at accessible sites of the antibody. By substituting those residues with cysteine, reactive thiol groups are thereby positioned at accessible sites of the bispecific antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521, 541.

Therefore, immunoconjugates of an anti-CD20/anti-CD3 bispecific antibody conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes, are specifically contemplated.

In some instances, an immunoconjugate is an antibody-drug conjugate (ADC) in which an bispecific antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some instances, an immunoconjugate comprises the bispecific antibody conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an the bispecific antibody conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of the anti-CD20/anti-CD3 bispecific antibody and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94111026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992): U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), which are commercially available (e.g., from Pierce Biotechnology, Inc., Rockford, Ill., U.S.A).

e. Other Antibody Derivatives

In some instances, an anti-CD20/anti-CD3 bispecific antibody may be modified to contain additional nonproteinaceous moieties that are known in the art and readily available and administered to the subject in accordance with the methods described herein. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylenemaleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some instances, conjugates of an antibody and nonproteinaceous moiety that may be selectively heated by exposure to radiation are provided. In one instance, the nonproteinaceous moiety is a carbon nanotube (Karn et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Pharmaceutical Compositions and Formulations

Pharmaceutical compositions and formulations of the anti-CD20/anti-CD3 bispecific antibodies can be prepared by mixing such antibodies having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanase such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

III. Articles of Manufacture

In another aspect of the invention, an article of manufacture containing materials useful for the treatment, prevention, and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an anti-CD20/anti-CD3 bispecific antibody described herein. The label or package insert indicates that the composition is used for treating the condition of choice (e.g., a B cell proliferation disorder, e.g., non-Hodgkin's lymphoma (NHL), e.g., diffuse large B cell lymphoma (DLBCL), e.g., relapsed or refractory DLBCL) and further includes information related to at least one of the dosing regimens described herein. Moreover, the article of manufacture may comprise (a) a first container with a composition contained therein, wherein the composition comprises an anti-CD20/anti-CD3 bispecific antibody described herein; and (b) a second container with a composition contained therein, wherein the composition comprises a further cytotoxic or otherwise therapeutic agent. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

IV. Examples

The following are examples of the methods of the invention. It is understood that various other embodiments may be practiced, given the general description provided above.

Example 1. Fractionated, Dose-Escalation Dosing Regimens for Treatment of B Cell Proliferation Disorders with Anti-Cluster of Differentiation 20 (CD20)/Anti-Cluster of Differentiation 3 (CD3) Bispecific Antibodies A full-length, IgG1 bispecific antibody that binds both CD20 and CD3 was generated using "knob-in-hole" engineering (see, e.g., U.S. Pat. No. 5,731,168). The safety and pharmacodynamics (PD) were consistent with its proposed mechanism of action in toxicology studies in cynomolgus monkeys. The toxicities associated with treatment with the anti-CD20/anti-CD3 bispecific antibody were largely driven by stimulation of T cells, as evidenced by PD changes in cytokine levels and activated T cell numbers. In repeat-dose toxicity studies in cynomolgus monkeys with the anti-CD20/anti-CD3 bispecific antibody, the increase of cytokine levels, T-cell activation, and acute post-dose observations were primarily limited to the first dose and were reduced or negligible following subsequent doses. Therefore, clinical strategies were designed to control the extent of T-cell stimulation through alternative dosing regimens.

In previous dosing studies, the anti-CD20/anti-CD3 bispecific antibody was dosed in a non-fractionated manner during Cycle 1, with the entirety of the dose being given on Cycle 1, Day 1 (C1D1). Preclinical data with the anti-CD20/anti-CD3 bispecific antibody indicated that double-step fractionation had the potential to decrease the risk of cytokine-driven toxicities. Therefore, we modified the protocol to administer the anti-CD20/anti-CD3 bispecific antibody in the context of a double-step fractionated, dose-escalation dosing schedule in Cycle 1.

To support this fractionated dosing schedule with the anti-CD20/anti-CD3 bispecific antibody, an exploratory quantitative systems pharmacology (QSP) model was used to simulate the time course of systemic cytokine (IL6) and activated T cell profiles in Cycle 1 following administration of the anti-CD20/anti-CD3 bispecific antibody as a single agent, using various dosing regimens of the anti-CD20/anti-CD3 bispecific antibody in patients with non-Hodgkin's lymphoma (NHL). Model-based predictions of serum cytokine concentrations and activated T cell time profiles following two cycles of treatment with the anti-CD20/anti-CD3 bispecific antibody as a single agent were used to compare non-fractionated and double-step fractionated dose schedules. The modeling and simulation support achieving a more favorable benefit-risk profile through a double-step fractionated, dose-escalation dosing regimen for treating hematologic cancers, such as B cell proliferation disorders (e.g., NHL, e.g., DLBCL), with the anti-CD20/anti-CD3 bispecific antibody. Based on the above, the double-step fractionated, dose-escalation dosing regimen is expected to reduce or inhibit cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities.

The double-step fractionated, dose-escalation dosing regimen commences with a dose-escalating first dosing cycle (C1), in which patients receive the anti-CD20/anti-CD3 bispecific antibody on Days 1, 8, and 15 of Cycle 1 (C1D1, C1D8, and C1D15, respectively). In Cycle 2 and beyond, the bispecific antibody is given as a single dose only on Day 1 of each 21-day cycle, with Day 1 of Cycle 2 (C2D1) being approximately 7 days after the C1D15 dose. In Cycle 2 and beyond, in which the bispecific antibody is given as a single dose only on Day 1 of each 21-day cycle, the bispecific antibody may be concurrently administered on Day 1 of each 21-day cycle with atezolizumab. The anti-CD20/anti-CD3 bispecific antibody and atezolizumab may be given up to ±2 days from the scheduled date (i.e., with a minimum of 19 days between doses) for logistic/scheduling reasons.

The cumulative Cycle 1 dose is about 50% greater than the highest cleared dose of the first cycle of a non-fractionated, dose-escalation dosing regimen, with the starting C1D15 dose corresponding to the highest cleared dose of the first cycle of the non-fractionated, dose-escalation dosing regimen. The C1D15 dose is the dose level administered on Day 1 of subsequent cycles (Cycle 2 through the terminal dosing cycle). This dose escalation uses a standard 3+3 design.

Example 2. Management of Cytokine Release Syndrome (CRS) with an Anti-Interleukin-6 Receptor (IL-6R) Antibody In the event that CRS is observed in patients who are administered an anti-CD20/anti-CD3 bispecific antibody in the context of the double-step fractionated, dose-escalation dosing regimen described in Example 1, the observed CRS should be managed appropriately.

CRS can result in significant disability or death if unsuccessfully managed. Current clinical management focuses on treating the individual signs and symptoms, providing supportive care, and attempting to dampen the inflammatory response using a high dose of corticosteroids. However, this approach is not always successful, especially in the case of late intervention. CRS observed in patients during the double-step fractionated, dose-escalation dosing regimen may be alternatively managed.

CRS is associated with elevations in a wide array of cytokines, including marked elevations in IFNγ, IL-6, and TNF-α levels. Emerging evidence implicates IL-6, in particular, as a central mediator in CRS. IL-6 is a proinflammatory, multi-functional cytokine produced by a variety of cell types, which has been shown to be involved in a diverse array of physiological processes, including T cell activation. Regardless of the inciting agent, CRS is associated with high IL-6 levels (Nagorsen et al. *Cytokine.* 25(1): 31-5, 2004; Lee et al. *Blood.* 124(2): 188-95, 2014); Doesegger et al. *Clin. Transl. Immunology.* 4(7): e39, 2015), and IL-6 correlates with the severity of CRS, with patients who experience a grade 4 or 5 CRS event having much higher IL-6 levels compared to patients who do not experience CRS or experience milder CRS (grades 0-3) (Chen et al. *J. Immunol. Methods.* 434:1-8, 2016). Therefore, blocking the inflammatory action of IL-6 using an agent that inhibits IL-6-mediated signaling to manage CRS observed in patients during the double-step fractionated, dose-escalation dosing regimen is an alternative to steroid treatment that would not be expected to negatively impact T cell function or diminish the efficacy or clinical benefit of anti-CD20/anti-CD3 bispecific antibody therapy in the treatment of B cell proliferative disorders.

Tocilizumab (ACTEMRA®/RoACTEMRA®) is a recombinant, humanized, anti-human monoclonal antibody directed against soluble and membrane-bound IL-6R, which inhibits IL-6-mediated signaling (see, e.g., WO 1992/019579, which is incorporated herein by reference in its entirety).

In the event of a grade 1 CRS event, management can be accomplished without tocilizumab therapy, with the CRS symptoms treated symptomatically using, for example, antihistamines, antipyretics, and/or analgesics as needed. In addition, fever and neutropenia is treated, if present, and the patient is monitored for fluid balance, with intravenous fluids administered as clinically indicated.

A grade 2 CRS event is managed in a patient having no (or minimal) comorbidities by following the management scheme for grade 1 CRS events and immediately suspending (i.e., delaying dosing) anti-CD20/anti-CD3 bispecific antibody treatment temporarily until CRS symptoms have resolved to grade ≤1 for three consecutive days, at which point the patient may receive the next dose of the anti-CD20/anti-CD3 bispecific antibody without dose reduction with the approval of the medical monitor. Cardiac and other organ function is carefully monitored in patients with grade 2 CRS, and oxygen is given for hypoxia, as needed. If there is no clinical improvement within 24 hours, the medical monitor should be notified and tocilizumab can be administered intravenously to the patient as a single dose at 8 mg/kg. A grade 2 CRS event is managed in a patient having extensive comorbidities by following the management scheme for a grade 3 CRS event described below.

In the event of a grade 3 CRS event, the medical monitor is immediately notified. Cardiopulmonary and organ function are monitored, oxygen is given for hypoxia, and hemodynamic support and other supportive care (e.g., for fever and/or neutropenia) is provided, as needed. In addition, anti-CD20/anti-CD3 bispecific antibody treatment is immediately suspended and the patient is administered tocilizumab intravenously at 8 mg/kg. If there is no clinical improvement within 24 hours, a second dose of tocilizumab is administered intravenously to the patient at 8 mg/kg, optionally in combination with the initiation of intravenous corticosteroid treatment (e.g., methylprednisolone at 2 mg/kg/day or dexamethasone at 10 mg for neurologic symptoms). Dosing of the anti-CD20/anti-CD3 bispecific antibody can be delayed for up to two weeks in order for the patient to recover from the CRS toxicity. If, following tocilizumab administration, CRS symptoms have resolved to grade ≤1 within two weeks, then dosing of the anti-CD20/anti-CD3 bispecific antibody is continued at a reduced dose. The reduced dose of the anti-CD20/anti-CD3 bispecific antibody is the next highest cleared dose level assessed during dose escalation (i.e., in the non-fractionated, dose-escalation dosing regimen). If similar toxicity is observed at the reduced dose, then anti-CD20/anti-CD3 bispecific antibody treatment is discontinued. In addition, if the reduced dose is below the pharmacodynamics activity range of the anti-CD20/anti-CD3 bispecific antibody, then anti-CD20/anti-CD3 bispecific antibody treatment may also be discontinued (i.e., permanently stopped).

A grade 4 CRS event is managed as described above for a grade 3 CRS event, but the anti-CD20/anti-CD3 bispecific antibody treatment is immediately discontinued (i.e., permanently stopped).

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating a subject having a B cell proliferative disorder comprising administering to the subject a full-length bispecific antibody that binds to CD20 and CD3 in a dosing regimen comprising at least a first three-dose 21-day dosing cycle, a second 21-day dosing cycle, and one or more additional 21-day dosing cycles, wherein:
   (a) the first three-dose 21-day dosing cycle comprises a first dose (C1 D1), a second dose (C1 D2), and a third dose (C1 D3) of the bispecific antibody, wherein the C1D1 and the C1D2 are each less than the C1D3, and wherein the C1D2 is greater than the C1 D1 by about 50% to about 250%, wherein the C1 D1 is between about 0.4 mg to about 4.0 mg, the C1 D2 is between about 1.0 mg to about 20.0 mg, and the C1 D3 is between about 1.0 mg to about 35 mg, and wherein the method comprises administering to the subject the C1 D1, the C1 D2, and the C1 D3 on or about Days 1, 8, and 15, respectively, of the first 21-day dosing cycle;
   (b) the second 21-day dosing cycle comprises a single dose (C2D1) of the bispecific antibody, wherein the C2D1 is equal to or greater than the C1 D3 and is between about 1.0 mg to about 35 mg, and wherein the method comprises administering to the subject the C2D1 on Day 1 of the second 21-day dosing cycle; and
   (c) each of the one or more additional 21-day dosing cycles comprises a single dose of the bispecific antibody, wherein each of the single doses of the bispecific antibody of the one or more additional 21-day dosing cycles is about equal in amount to the C2D1, and wherein the method comprises administering to the subject each of the one or more additional single doses on Day 1 of each of the one or more additional 21-day dosing cycles; and wherein the full-length bispecific antibody comprises:
   an anti-CD20 arm comprising a first binding domain comprising the following six hypervariable regions (HVRs):
      (i) an HVR-H1 comprising the amino acid sequence of GYTFTSYNMH (SEQ ID NO: 1);
      (ii) an HVR-H2 comprising the amino acid sequence of AIYPGNGDTSYNQKFKG (SEQ ID NO: 2);
      (iii) an HVR-H3 comprising the amino acid sequence of VVYYSNSYWYFDV (SEQ ID NO:3);
      (iv) an HVR-L1 comprising the amino acid sequence of RASSSVSYMH (SEQ ID NO: 4);
      (v) an HVR-L2 comprising the amino acid sequence of APSNLAS (SEQ ID NO: 5); and
      (vi) an HVR-L3 comprising the amino acid sequence of QQWSFNPPT (SEQ ID NO: 6); and
   an anti-CD3 arm comprising a second binding domain comprising the following six HVRs:
      (i) an HVR-H1 comprising the amino acid sequence of NYYIH (SEQ ID NO: 9);
      (ii) an HVR-H2 comprising the amino acid sequence of WIYPGDGNTKYNEKFKG (SEQ ID NO: 10);
      (iii) an HVR-H3 comprising the amino acid sequence of DSYSNYYFDY (SEQ ID NO: 11);
      (iv) an HVR-L1 comprising the amino acid sequence of KSSQSLLNSRTRKNYLA (SEQ ID NO: 12);
      (v) an HVR-L2 comprising the amino acid sequence of WASTRES (SEQ ID NO: 13); and
      (vi) an HVR-L3 comprising the amino acid sequence of TQSFILRT (SEQ ID NO: 14).

2. The method of claim 1, wherein:
   (a) the C1 D1 is between about 0.8 mg to about 3.0 mg, the C1 D2 is between about 1.0 mg to about 6.0 mg, and the C1 D3 is between about 3.0 to about 6.0 mg; and
   (b) the C2D1 is between about 3.0 to about 6.0 mg.

3. The method of claim 2, wherein:
(a) the C1 D1 is about 0.8 mg, the C1 D2 is about 2.0 mg, and the C1 D3 is about 4.2 mg, and the C2D1 is about 4.2 mg; or
(b) the C1 D1 is about 1.0 mg, the C1 D2 is about 1.0 mg, and the C1 D3 is about 3.0 mg, and the C2D1 is about 3.0 mg; or
(c) the C1 D1 is about 1.0 mg, the C1 D2 is about 2.0 mg, and the C1 D3 is about 6.0 mg, and the C2D1 is about 6.0 mg; or
(d) the C1 D1 is about 0.8 mg, the C1 D2 is about 2.0 mg, and the C1 D3 is about 6.0 mg, and the C2D1 is about 6.0 mg.

4. The method of claim 1, wherein the dosing regimen comprises one to fourteen additional 21-day dosing cycles.

5. The method of claim 1, wherein the bispecific antibody comprises an anti-CD20 arm comprising a first binding domain comprising (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b).

6. The method of claim 1, wherein the bispecific antibody comprises an anti-CD3 arm comprising a second binding domain comprising (a) a VH domain comprising an amino acid sequence having at least 95% sequence identity to the amino acid sequence of SEQ ID NO: 15; (b) a VL domain comprising an amino acid sequence having at least 95% sequence identity to the amino acid sequence of SEQ ID NO: 16; or (c) a VH domain as in (a) and a VL domain as in (b).

7. The method of claim 1, wherein the bispecific antibody comprises an aglycosylation site mutation.

8. The method of claim 7, wherein the aglycosylation site mutation reduces effector function of the bispecific antibody.

9. The method of claim 7, wherein the aglycosylation site mutation is a substitution mutation.

10. The method of claim 9, wherein the bispecific antibody comprises a substitution mutation in the Fc region that reduces effector function.

11. The method of claim 10, wherein the substitution mutation is at amino acid residue N297, L234, L235, and/or D265 (EU numbering).

12. The method of claim 11, wherein the substitution mutation is selected from the group consisting of N297G, N297A, L234A, L235A, D265A, and P329G.

13. The method of claim 1, wherein the bispecific antibody is a monoclonal antibody, a humanized antibody, or a chimeric antibody.

14. The method of claim 1, wherein the bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, a second CH2 ($CH2_2$) domain, and a second CH3 ($CH3_2$) domain.

15. The method of claim 14, wherein the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain.

16. The method of claim 15, wherein the $CH3_1$ and $CH3_2$ domains meet at an interface between the protuberance and cavity.

17. The method of claim 14, wherein the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain.

18. The method of claim 17, wherein the $CH2_1$ and $CH2_2$ domains meet at an interface between said protuberance and cavity.

19. The method of claim 1, wherein the bispecific antibody is administered to the subject as a monotherapy.

20. The method of claim 1, wherein the bispecific antibody is administered to the subject as a combination therapy.

21. The method of claim 20, wherein the bispecific antibody is administered to the subject concurrently with an additional therapeutic agent or prior to the administration of an additional therapeutic agent.

22. The method of claim 21, wherein the additional therapeutic agent is atezolizumab.

23. The method of claim 22, further comprising administering to the subject a first dose of atezolizumab concurrently with the C2D1 of the bispecific antibody on Day 1 of the second 21-day dosing cycle.

24. The method of claim 23, further comprising administering to the subject atezolizumab concurrently with the single dose of the bispecific antibody of the one or more additional 21-day dosing cycles on Day 1 of the one or more additional 21-day dosing cycles.

25. The method of claim 24, wherein atezolizumab is only administered to the subject concurrently with the bispecific antibody.

26. The method of claim 22, wherein each dose of atezolizumab is about 1200 mg.

27. The method of claim 20, wherein the bispecific antibody is administered to the subject subsequent to the administration of an additional therapeutic agent.

28. The method of claim 27, wherein the additional therapeutic agent is obinutuzumab or tocilizumab.

29. The method of claim 1, wherein the B cell proliferative disorder is a non-Hodgkin's lymphoma (NHL) or a chronic lymphoid leukemia (CLL).

30. The method of claim 29, wherein the NHL is a follicular lymphoma (FL), a diffuse-large B cell lymphoma (DLBCL), a mantle cell lymphoma (MCL), or a primary mediastinal (thymic) large B cell lymphoma (PMLBCL).

31. The method of claim 30, wherein the DLBCL is a relapsed or refractory DLBCL.

32. The method of claim 1, wherein the subject has a cytokine release syndrome (CRS) event, and the method further comprises treating the symptoms of the CRS event while suspending treatment with the bispecific antibody.

33. The method of claim 32, wherein the method further comprises administering to the subject an effective amount of tocilizumab to treat the CRS event.

34. The method of claim 33, wherein tocilizumab is administered intravenously to the subject as a single dose of about 8 mg/kg.

35. The method of claim 34, wherein the CRS event does not resolve or worsens within 24 hours of treating the symptoms of the CRS event, the method further comprising administering to the subject one or more additional doses of tocilizumab to manage the CRS event.

36. The method of claim 21, wherein the additional therapeutic agent is an antibody-drug conjugate (ADC).

37. The method of claim 36, wherein the ADC is an anti-CD79b ADC.

38. The method of claim 37, wherein the anti-CD79b ADC is polatuzumab vedotin.

39. A method of treating a subject having a B cell proliferative disorder comprising administering to the subject a full-length bispecific antibody that binds to CD20 and CD3 in a dosing regimen comprising at least a first three-dose 21-day dosing cycle, a second 21-day dosing cycle, and one or more additional 28-day dosing cycles, wherein:
(a) the first three-dose 21-day dosing cycle comprises a first dose (C1 D1), a second dose (C1 D2), and a third dose (C1 D3) of the bispecific antibody,
wherein the C1D1 and the C1 D2 are each less than the C1D3, and wherein the C1 D2 is greater than the C1D1 by about 50% to about 250%,
wherein the C1D1 is between about 0.4 mg to about 4.0 mg, the C1D2 is between about 1.0 mg to about 20.0 mg, and the C1D3 is between about 1.0 mg to about 35 mg, and
wherein the method comprises administering to the subject the C1D1, the C1D2, and the C1 D3 on or about Days 1, 8, and 15, respectively, of the first 21-day dosing cycle;
(b) the second 21-day dosing cycle comprises a single dose (C2D1) of the bispecific antibody, wherein the C2D1 is equal to or greater than the C1 D3 and is between about 1.0 mg to about 35 mg, and
wherein the method comprises administering to the subject the C2D1 on Day 1 of the second 21-day dosing cycle; and
(c) each of the one or more additional 28-day dosing cycles comprises a single dose of the bispecific antibody, wherein each of the single doses of the bispecific antibody of the one or more additional 28-day dosing cycles is about equal in amount to the C2D1, and
wherein the method comprises administering to the subject each of the one or more additional single doses on Day 1 of each of the one or more additional 28-day dosing cycles; and
wherein the full-length bispecific antibody comprises:
an anti-CD20 arm comprising a first binding domain comprising the following six hypervariable regions (HVRs):
(i) an HVR-H1 comprising the amino acid sequence of GYTFTSYNMH (SEQ ID NO: 1);
(ii) an HVR-H2 comprising the amino acid sequence of AIYPGNGDTSYNQKFKG (SEQ ID NO: 2);
(iii) an HVR-H3 comprising the amino acid sequence of VVYYSNSYWYFDV (SEQ ID NO:3);
(iv) an HVR-L1 comprising the amino acid sequence of RASSSVSYMH (SEQ ID NO: 4);
(v) an HVR-L2 comprising the amino acid sequence of APSNLAS (SEQ ID NO: 5); and
(vi) an HVR-L3 comprising the amino acid sequence of QQWSFNPPT (SEQ ID NO: 6); and
an anti-CD3 arm comprising a second binding domain comprising the following six HVRs:
(i) an HVR-H1 comprising the amino acid sequence of NYYIH (SEQ ID NO: 9);
(ii) an HVR-H2 comprising the amino acid sequence of WIYPGDGNTKYNEKFKG (SEQ ID NO: 10);
(iii) an HVR-H3 comprising the amino acid sequence of DSYSNYYFDY (SEQ ID NO: 11);
(iv) an HVR-L1 comprising the amino acid sequence of KSSQSLLNSRTRKNYLA (SEQ ID NO: 12);
(v) an HVR-L2 comprising the amino acid sequence of WASTRES (SEQ ID NO: 13); and
(vi) an HVR-L3 comprising the amino acid sequence of TQSFILRT (SEQ ID NO: 14).

40. The method of claim 39, wherein:
(a) the C1 D1 is between about 0.8 mg to about 3.0 mg, the C1 D2 is between about 1.0 mg to about 6.0 mg, and the C1 D3 is between about 3.0 to about 6.0 mg; and
(b) the C2D1 is between about 3.0 to about 6.0 mg.

41. The method of claim 40, wherein:
(a) the C1 D1 is about 0.8 mg, the C1 D2 is about 2.0 mg, and the C1 D3 is about 4.2 mg, and the C2D1 is about 4.2 mg; or
(b) the C1 D1 is about 1.0 mg, the C1 D2 is about 1.0 mg, and the C1 D3 is about 3.0 mg, and the C2D1 is about 3.0 mg; or
(c) the C1 D1 is about 1.0 mg, the C1 D2 is about 2.0 mg, and the C1 D3 is about 6.0 mg, and the C2D1 is about 6.0 mg; or
(d) the C1 D1 is about 0.8 mg, the C1 D2 is about 2.0 mg, and the C1 D3 is about 6.0 mg, and the C2D1 is about 6.0 mg.

42. The method of claim 39, wherein the dosing regimen comprises one to fourteen additional 28-day dosing cycles.

43. The method of claim 39, wherein the bispecific antibody comprises an anti-CD20 arm comprising a first binding domain comprising (a) a heavy chain variable (VH) domain comprising an amino acid sequence having at least 95% sequence identity to the amino acid sequence of SEQ ID NO: 7; (b) a light chain variable (VL) domain comprising an amino acid sequence having at least 95% sequence identity to the amino acid sequence of SEQ ID NO: 8; or (c) a VH domain as in (a) and a VL domain as in (b).

44. The method of claim 39, wherein the bispecific antibody comprises an anti-CD3 arm comprising a second binding domain comprising (a) a VH domain comprising an amino acid sequence having at least 95% sequence identity to the amino acid sequence of SEQ ID NO: 15; (b) a VL domain comprising an amino acid sequence having at least 95% sequence identity to the amino acid sequence of SEQ ID NO: 16; or (c) a VH domain as in (a) and a VL domain as in (b).

45. The method of claim 39, wherein the bispecific antibody comprises an aglycosylation site mutation.

46. The method of claim 45, wherein the aglycosylation site mutation reduces effector function of the bispecific antibody.

47. The method of claim 45, wherein the aglycosylation site mutation is a substitution mutation.

48. The method of claim 47, wherein the bispecific antibody comprises a substitution mutation in the Fc region that reduces effector function.

49. The method of claim 48, wherein the substitution mutation is at amino acid residue N297, L234, L235, and/or D265 (EU numbering).

50. The method of claim 49, wherein the substitution mutation is selected from the group consisting of N297G, N297A, L234A, L235A, D265A, and P329G.

51. The method of claim 39, wherein the bispecific antibody is a monoclonal antibody, a humanized antibody, or a chimeric antibody.

52. The method of claim 39, wherein the bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, a second CH2 ($CH2_2$) domain, and a second CH3 ($CH3_2$) domain.

53. The method of claim 52, wherein the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain.

54. The method of claim 53, wherein the $CH3_1$ and $CH3_2$ domains meet at an interface between the protuberance and cavity.

55. The method of claim 52, wherein the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain.

56. The method of claim 55, wherein the $CH2_1$ and $CH2_2$ domains meet at an interface between said protuberance and cavity.

57. The method of claim 39, wherein the bispecific antibody is administered to the subject as a monotherapy.

58. The method of claim 39, wherein the bispecific antibody is administered to the subject as a combination therapy.

59. The method of claim 58, wherein the bispecific antibody is administered to the subject concurrently with an additional therapeutic agent or prior to the administration of an additional therapeutic agent.

60. The method of claim 59, wherein the additional therapeutic agent is atezolizumab.

61. The method of claim 60, further comprising administering to the subject a first dose of atezolizumab concurrently with the C2D1 of the bispecific antibody on Day 1 of the second 21-day dosing cycle.

62. The method of claim 61, further comprising administering to the subject atezolizumab concurrently with the single dose of the bispecific antibody of the one or more additional 28-day dosing cycles on Day 1 of the one or more additional 28-day dosing cycles.

63. The method of claim 62, wherein atezolizumab is only administered to the subject concurrently with the bispecific antibody.

64. The method of claim 60, wherein each dose of atezolizumab is about 1200 mg.

65. The method of claim 58, wherein the bispecific antibody is administered to the subject subsequent to the administration of an additional therapeutic agent.

66. The method of claim 65, wherein the additional therapeutic agent is obinutuzumab or tocilizumab.

67. The method of claim 39, wherein the B cell proliferative disorder is a non-Hodgkin's lymphoma (NHL) or a chronic lymphoid leukemia (CLL).

68. The method of claim 67, wherein the NHL is a follicular lymphoma (FL), a diffuse-large B cell lymphoma (DLBCL), a mantle cell lymphoma (MCL), or a primary mediastinal (thymic) large B cell lymphoma (PMLBCL).

69. The method of claim 68, wherein the DLBCL is a relapsed or refractory DLBCL.

70. The method of claim 39, wherein the subject has a cytokine release syndrome (CRS) event, and the method further comprises treating the symptoms of the CRS event while suspending treatment with the bispecific antibody.

71. The method of claim 70, wherein the method further comprises administering to the subject an effective amount of tocilizumab to treat the CRS event.

72. The method of claim 71, wherein tocilizumab is administered intravenously to the subject as a single dose of about 8 mg/kg.

73. The method of claim 72, wherein the CRS event does not resolve or worsens within 24 hours of treating the symptoms of the CRS event, the method further comprising administering to the subject one or more additional doses of tocilizumab to manage the CRS event.

74. The method of claim 59, wherein the additional therapeutic agent is an antibody-drug conjugate (ADC).

75. The method of claim 74, wherein the ADC is an anti-CD79b ADC.

76. The method of claim 75, wherein the anti-CD79b ADC is polatuzumab vedotin.

77. The method of claim 4, wherein the dosing regimen comprises six additional 21-day dosing cycles.

78. The method of claim 4, wherein the dosing regimen comprises eight additional 21-day dosing cycles.

79. The method of claim 42, wherein the dosing regimen comprises six additional 28-day dosing cycles.

80. The method of claim 42, wherein the dosing regimen comprises eight additional 28-day dosing cycles.

81. The method of claim 1, wherein the C1D1 is about 1 mg and the C1D2 is about 2 mg.

82. The method of claim 39, wherein the C1D1 is about 1 mg and the C1D2 is about 2 mg.

* * * * *

SEQUENCE LISTING

```
<160> NUMBER OF SEQ ID NOS: 42

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Ser Tyr Asn Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Ala Ile Tyr Pro Gly Asn Gly Asp Thr Ser Tyr Asn Gln Lys Phe Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Val Val Tyr Tyr Ser Asn Ser Tyr Trp Tyr Phe Asp Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Arg Ala Ser Ser Ser Val Ser Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Pro Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 6

Gln Gln Trp Ser Phe Asn Pro Pro Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
        50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
                100                 105                 110

Gly Gln Gly Thr Leu Val Thr Val Ser Ser
            115                 120

<210> SEQ ID NO 8
<211> LENGTH: 106
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
                20                  25                  30

His Trp Tyr Gln Gln Lys Pro Gly Lys Ala Pro Lys Pro Leu Ile Tyr
            35                  40                  45

Ala Pro Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct
```

<400> SEQUENCE: 9

Asn Tyr Tyr Ile His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Trp Ile Tyr Pro Gly Asp Gly Asn Thr Lys Tyr Asn Glu Lys Phe Lys
1               5                   10                  15

Gly

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Asp Ser Tyr Ser Asn Tyr Tyr Phe Asp Tyr
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Lys Ser Ser Gln Ser Leu Leu Asn Ser Arg Thr Arg Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Trp Ala Ser Thr Arg Glu Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Thr Gln Ser Phe Ile Leu Arg Thr
1               5

<210> SEQ ID NO 15
<211> LENGTH: 119
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

```
<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Trp Val Arg Gln Ala Pro Gly Lys Gly Leu Glu Trp Val Gly
1               5                   10

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Arg Phe Thr Ile Ser Val Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Trp Gly Gln Gly Thr Leu Val Thr Val Ser Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Trp Tyr Gln Gln Lys Pro Gly Lys Ala Pro Lys Pro Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct
```

```
<400> SEQUENCE: 23

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Phe Gly Gln Gly Thr Lys Val Glu Ile Lys
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
                20                  25                  30

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Trp Val Arg Gln Ala Pro Gly Gln Gly Leu Glu Trp Ile Gly
1               5                   10

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Arg Ala Thr Leu Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
                20                  25                  30

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Trp Gly Gln Gly Thr Leu Val Thr Val Ser Ser
1               5                   10
```

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp Tyr Gln Gln Lys Pro Gly Gln Pro Pro Lys Leu Leu Ile Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Phe Gly Gln Gly Thr Lys Val Glu Ile Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Gly Phe Thr Phe Ser Asp Ser Trp Ile His
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Synthetic Construct

```
<400> SEQUENCE: 34

Ala Trp Ile Ser Pro Tyr Gly Gly Ser Thr Tyr Tyr Ala Asp Ser Val
1               5                   10                  15

Lys Gly

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Arg His Trp Pro Gly Gly Phe Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Arg Ala Ser Gln Asp Val Ser Thr Ala Val Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ser Ala Ser Phe Leu Tyr Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln Gln Tyr Leu Tyr His Pro Ala Thr
1               5

<210> SEQ ID NO 39
<211> LENGTH: 118
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
            35                  40                  45
```

```
Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ser
            115

<210> SEQ ID NO 40
<211> LENGTH: 108
<212> TYPE: PRT
<213> ORGANISM: Artificial Sequence
<220> FEATURE:
<223> OTHER INFORMATION: Synthetic Construct

<400> SEQUENCE: 40

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg
            100                 105

<210> SEQ ID NO 41
<211> LENGTH: 447
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Ser
                 20                  25                  30

Trp Ile His Trp Val Arg Gln Ala Pro Gly Lys Gly Leu Glu Trp Val
             35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ser Ala Ser Thr Lys Gly Pro Ser Val Phe Pro
            115                 120                 125
```

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 42
<211> LENGTH: 214
<212> TYPE: PRT
<213> ORGANISM: Artificial Sequence
<220> FEATURE:
<223> OTHER INFORMATION: Synthetic Construct

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

```
Tyr Ser Ala Ser Phe Leu Tyr Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Leu Tyr His Pro Ala
            85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
    210
```